US005622824A

United States Patent [19]

Köster

[11] Patent Number: 5,622,824
[45] Date of Patent: Apr. 22, 1997

[54] DNA SEQUENCING BY MASS SPECTROMETRY VIA EXONUCLEASE DEGRADATION

[75] Inventor: Hubert Köster, Concord, Mass.

[73] Assignee: Sequenom, Inc., Boston, Mass.

[21] Appl. No.: 388,171

[22] Filed: Feb. 10, 1995

Related U.S. Application Data

[63] Continuation of Ser. No. 34,738, Mar. 19, 1993, abandoned.
[51] Int. Cl.$^6$ .............................. C12Q 1/68; B01D 59/44; G01N 30/72
[52] U.S. Cl. .............................. 435/6; 250/282; 250/288; 422/68.1
[58] Field of Search .............................. 435/6; 250/282, 250/288; 422/68.1

[56] References Cited

U.S. PATENT DOCUMENTS

| | | | |
|---|---|---|---|
| 4,997,928 | 3/1991 | Hobbs, Jr. | 536/24.3 |
| 5,002,868 | 3/1991 | Jacobson et al. | 536/25.32 |
| 5,174,962 | 12/1992 | Brennan | 422/78 |
| 5,288,644 | 2/1994 | Beavis et al. | 436/94 |

FOREIGN PATENT DOCUMENTS

| | | |
|---|---|---|
| 0359225 | 3/1990 | European Pat. Off. . |
| 0360677 | 3/1990 | European Pat. Off. . |
| 0360676 | 3/1990 | European Pat. Off. . |
| 0371437 | 6/1990 | European Pat. Off. . |
| 3930312 | 4/1990 | Germany . |
| 4011991 | 10/1990 | Germany . |
| WO89/03432 | 4/1989 | WIPO . |
| WO89/09282 | 10/1989 | WIPO . |
| WO89/12694 | 12/1989 | WIPO . |
| WO90/14148 | 11/1990 | WIPO . |
| WO90/15883 | 12/1990 | WIPO . |
| WO91/05060 | 4/1991 | WIPO . |
| WO91/06678 | 5/1991 | WIPO . |
| WO91/11533 | 8/1991 | WIPO . |
| WO92/02635 | 2/1992 | WIPO . |
| WO92/03575 | 3/1992 | WIPO . |

OTHER PUBLICATIONS

Jacobson, K. Bruce et al., "Applications of Mass Spectrometry to DNA Sequencing", GATA, 8(8) pp. 223–229 (1991).
Ardrey "Electrospray Mass Spectrometry" Spectroscopy Europe 1992, vol. 4, No. 4, pp. 11–18.
Axelrod et al. "Transcription from Bacteriophage T7 and SP6 RNA Polymerase Promoters in the Presence of 3'-Deoxyribonucleoside 5'-Ttiphosphate Chain Terminators" Biochemistry 1985, vol. 24, pp. 5716–5723.
Arlinghaus et al. "Applications of resonance ionization spectroscopy for semiconductor, environmental and biomedical analysis, and for DNA sequencing" SPIE 1991, vol. 1435, pp. 26–35.
Bains "Setting a Sequence to Sequence a Sequence" BIO/Technology 1992, vol. 10, pp. 757–758.
Bains "DNA Sequencing by Mass Spectrometry. Outline of a Potential Future Application" ChimicaOggi Review 1991, vol. Oct.

Barrell "DNA sequencing: present limitations and prospects for the future" The FASEB Journal 1991, vol. 5, pp. 40–45.
Beck et al. "Applications of Dioxetane Chemiluminescent Probes to Molecular Biology" Analytical Chemistry 1990, vol. 17, No. 21, pp. 2258–2270.
Beck et al. "Chemiluminescent detection of DNA: application for DNA sequencing and hybridization" Nucleic Acid Research 1989, vol. 17, No. 13, pp. 5115–5123.
Brennan et al. "New Methods to Sequence DNA by Mass Spectrometry" SPIE/New Technologies in Cytometry and Molecular Biology 1990, vol. 1206, pp. 60–67.
Brumbaugh et al. "Continous, on–line DNA sequencing using oligodeonucleotide primers with multiple fluorophores" PNAS 1988, vol. 85, pp. 5610–5614.
Chu et al. "Synthesis of an amplifiable reporter RNA for bioassays" Nucleic Acid Research 1986, vol. 14 No. 14, pp. 5590–5603.
Church et al. "Multiplex DNA Sequencing" Science Research Articles 1988, vol. 240, pp. 185–188.
Covey et al. "The Determination of Protein, Oligonucleotide and Peptide Molecular Weights by Ion–spray Mass Spectrometry" Rapid Communications in Mass Spectrometry 1988, vol. 2, No. 11, pp. 249–256.
Crain "Mass spectrometrc techniques in nucleic acid research" Mass Spectrometry Reviews 1990, vol. 9, pp. 505–554.
Edmonds et al. "Electrospray Ionization Mass Spectrometry" Methods in Enzymology 1990, vol. 193, pp. 412–431.
Eckstein (editor) "Oligonucleotides and Analogues: A Practical Approach" 1991, Chapter 7, by Connolly, pp. 155–183.
Eckstein "Nucleoside Phosphorothioates" Ann. Rev. Biochem. 1985, vol. 54, pp. 367–402.
Eckstein "Phosphorothioate Analogues of Nucleotides" Accounts of Chemical Research 1978, vol. 12, pp. 204–210.
Eckstein et al. "Synthesis and Properties of Diastereoisomers of Adenosine 5'–(O–1–Thiotriphosphate) and Adenoise 5'–(O–2–Thiotriphosphate)" Biochemistry 1976, vol. 15, No. 8, pp. 1685–1691.
Fehere et al. "Matrix–assisted Laser Desorption Mass Spectrometry of Oligodeoxythymidylic Acids" Rapid Communications in Mass Spectrometry 1992, vol. 6, pp. 209–213.
Frank et al. "DNA chain length and the influence of base composition on electrophoretic mobility of oligodeoxyribonucleotides in polyacrylamide–gels" Nucleic Acid Research 1979, vol. 6, No. 6, pp. 2069–2087.

(List continued on next page.)

*Primary Examiner*—Mindy Fleisher
*Assistant Examiner*—Thanda Wai
*Attorney, Agent, or Firm*—Lahive & Cockfield; Beth E. Arnold, Esq.; Giulio A. DeConti, Jr.

[57] ABSTRACT

Methods for determining the sequence of nucleic acids by cleaving the nucleic acid unilaterally from a first end with an exonuclease activity to sequentially release individual nucleotides, identifying each of the sequentially release nucleotides by mass spectrometry, and determining the sequence of the nueleic acid from the identified nucleotides are disclosed. The method is amenable to multiplexing for simultaneously determining more than one nucleic acid sequence.

28 Claims, 14 Drawing Sheets

OTHER PUBLICATIONS

Gildea et al. "A Versatile Acid–labile Linker for Modification of Synthetic Biomolecules" Tetrahedron Letters 1990, vol. 31, No. 49, pp. 7095–7098.

Green et al. "Variable–wavelength On–column Fluorescence Detector for Open–tubular Zone Electrophoresis" Journal of Chromatography 1986, vol. 352, pp. 337–343.

Haralambidis et al. "Preparation of base–modified nucleosides suitable for non–radioactive label attachment and their incorporation into synthetic oligodeoxyribonucleotides" Nucleic Acid Research 1987, vol. 15, No. 12, pp. 4857–4876.

Khrapko et al. "An oligonucleotide hybridization approach to DNA sequencing" FEBS Letters 1989, vol. 256, No. 1,2, pp. 118–122.

Higuchi et al. "A general method of in vitro preparation and specific mutagenesis of DNA fragments: study of protein and DNA interactions" Nucleic Acid Research 1988, vol. 16, No. 15, pp. 7351–7367.

Hillenkamp et al. "Matrix–Assisted UV–Laser Desorption/Ionization: A New Approach to Mass Spectrometry of Large Biomolecules" Biological Mass Spectrometry 1987, pp. 49–61.

Hobbs et al. "A General Method for the Synthesis of 2'–Azido–2'–deoxy–and 2'–Amino–2'–deoxyribofuranosyl Purines" Journal Organic Chemistry 1977, vol. 42, No. 4, pp. 714–719.

Hyman "A New Method of Sequencing DNA" Analytical Biochemistry 1988, vol. 174, pp. 423–436.

Koster et al. "Oligonucleotide synthesis and multiplex DNA sequencing using chemiluminescent detection" Nucleic Acid Research Symposioum Series 1991, No. 24, pp. 318–321.

Koster et al. "N–Acyl Protecting Groups for Deoxynucleosides a Quantitative and Comparative Study" Tetrahedron 1981, vol. 37, No. 2, pp. 363–369.

Ikehara et al. "Studies of Nucleosides and Nucleotides LXXIX. Purine Cyclonucleosides. (37). The Total Synthesis of an Antibiotic 2'–Amino–2'–deoxyguanosine" Chem. Pharm. Bull. 1978, vol. 26, No. 1, pp. 240–244.

Imazawa et al. "Facile Synthesis of 2'–Amino–2'–deoxyribofuranosyl Purines" Journal Organic Chemistry 1979, vol. 44, No. 12, pp. 2039–2041.

Jett et al. "High–Speed DNA Sequencing: An Approach Based Upon Fluorescence Detection of Single Molecules" Journal of Biomolecular Structure & Dynamics 1989, vol. 7, No. 2, pp. 301–309.

Lim et al. "Optimal Conditions for Supercoil DNA Sequencing with the *Eschirichia coli*DNA Polymerase I Large Fragment" Gene. Anal. Techn. 1988, vol. 5, pp. 32–39.

Nakamaye et al. "Direct sequencing of polymerase chain reaction amplified DNA fragments through the incorporation of deoxynucleoside o–thitriphosphates" Nucleic Acid Research 1988 vol. 16, No. 21, pp. 9947–9959.

Nelson et al. "Time–of–Flight Mass Spectrometry of Nucleic Acids by Laser Ablation and Ionization from A Frozen Aqueous Matrix" Rapid Communications In Spectrometry 1990, vol. 4, No. 9, pp. 348–351.

Nelson et al. "Volatization of High Molecular Weight DNA by Pulsed Laser Ablation of Frozen Aqueous Solutions" Science Reports 1989, vol. 246, pp. 1585–1587.

Perrouault et al. "Sequence–specific artificial photo–induced endonucleases based on triple helix–forming oligonucleotides" Nature (Letters to Nature) 1990, vol. 344, pp. 358–360.

Pitulle et al. "Initiator oligonucleotides for the combination of chemical and enzymatic RNA synthesis" Gene 1992, vol. 112, pp. 101–105.

Prober et al. "A System for Rapid DNA Sequencing with Fluorescent Chain–Terminating Dideoxynucleotides" Science Research Articles 1987, vol. 238, pp. 336–341.

Schram et al. "Mass Spectrometry of Nucleic Acd Components" Mathods Biochem. Anal. 1990, vol. 34, pp. 203–287.

Seela et al. "98. 1,7–Dideaza–2', 3'–dideoxyadenosine: Syntheses of Pyrrolo[2,3–b]pyridine 2', 3'–Dideoxyribofuranosides and Participation of Purine N(1) during HIV–1 Reverse Transcriptase Inhibition" Helvetica Chimica Acta 1991, vol. 74, pp. 1048–1058.

Singh et al. "Oligonucleotides, part 5+: synthesis and fluorescence studies of DNA oligomers d(AT)5 containing adenines covalently linked at C–8 with dansyl flurophore" Nucleic Acid Research 1990, vol. 18, No. 11, pp. 3339–3345.

Sinha et al. "Polymer support oligonucleotide synthesis XVIII: use of B–cyanoethyl–N, N–dialklyamino–/N–morpholino phosphoramidite of deoxynucleosides for the synthesis of DNA fragments simplifying deprotection and isolation of final product" Nuc. Acid Res. 1984, vol. 12 No. 11 pp. 4539–4557.

Slim et al. "Configurationally defined phosphorothioate–containing oligoribonucleotides in the study of the mechanism of cleavage of hammerhead ribozymes" Nucleic Acid Research 1991, vol. 19, No. 6 pp. 1183–1188.

Smith et al. "New Developments in Biochemical Mass Spectrometry: Electrospray Ionization" Anal. Chem. 1990, vol. 62, pp. 882–899.

Smith et al. "Fluorescence detection in automated DNA sequence analysis" Nature 1986, vol. 321, pp. 674–679.

Sowa et al. "The Facile Synthesis of 5'–Nucleotides by the Selective Phosphorylation of a Primary Hydroxyl Group of Nucleosides with Phosphoryl Chloride" Bulletin of the Chemical Society of Japan 1975, vol. 48, No. 7, pp. 2084–2090.

Sproat et al. "The synthesis of protected 5'–mercapto–2', 5'–dideoxyribonucleoside–3'–O–phosphorarmidites; uses of 5'–mercapto–oligodeoxyribonucleotides" Nucleic Acid Research 1987, vol. 15, No. 12, pp. 4837–4848.

Sproat et al. "The synthesis of protected 5'–amino–2', 5'dideoxyribonucleoside–3'–phosphoramidites; applications of 5'–amino–oligodeoxyribonucleotides" Nucleic Acid Research 1987, vol. 15, No. 15, pp. 6181–6196.

Still et al. "Rapid Chromatographic Technique for Preparative Separations with Moderate Resolution" Journal Organic Chemistry 1978, vol. 43, No. 14, pp. 2923–2925.

Swerdlow et al. "Capillary gel electrophoresis for rapid, high resolution DNA sequencing" Nucleic Acid Research 1990, vol. 18, No. 6, pp. 1415–1419.

Trainor et al. "DNA Sequencing, Automation, and the Human Genome" Anal. Chem. 1990, vol. 62, pp. 418–426.

Verheyden et al. "Synthesis of Some Pyrimidine 2'–Amino–2'–deoxynucleosides" Journal Organic Chemistry 1971, vol. 36, No. 2, pp. 250–254.

Wolter et al. "Negative Ion FAB Mass Spectrometry Analysis of Non–charged Key Intermediates in Oligonucleotide Synthesis: Rapid Identification of Partially Protected Dinucleoside Monophosphates" Biomedical and Enviromental Mass Spectrometry 1987, vol. 14, pp. 111–116.

Yamashita et al. "Electrospray Ion Source. Another Variation on the Free–Jet Theme" J. Phys. Chem. 1984, vol 88, pp. 4451–4459.

$n = 1 - 1000$

M = H, OH, XR, Halogen, $N_3$

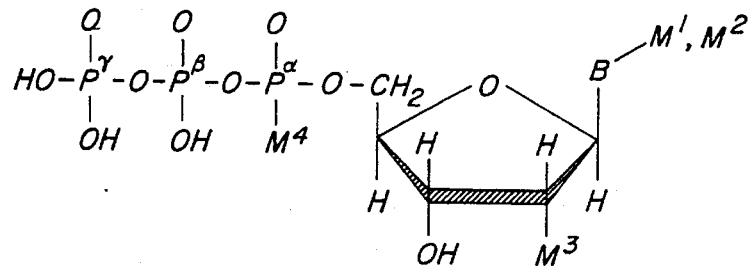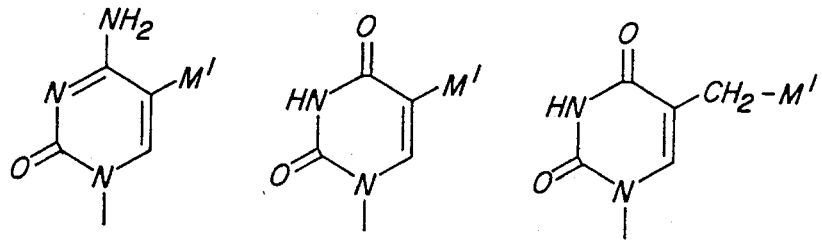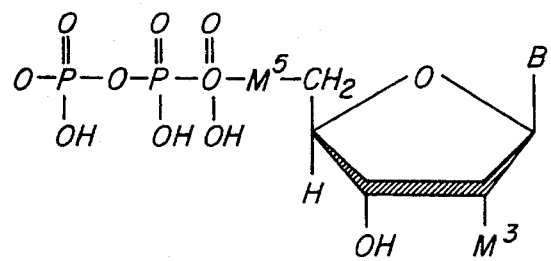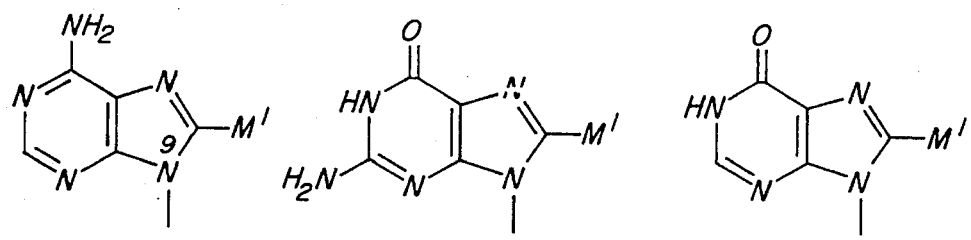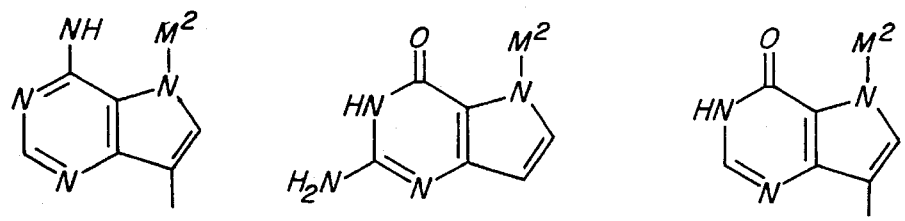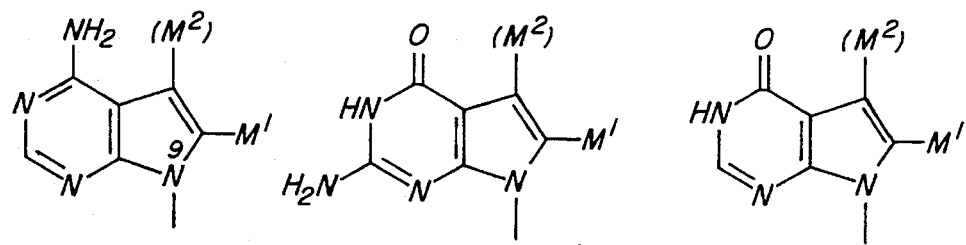
$M^1, M^2$ or $M^3$ = H, OH, XR, R, Halogen, $N_3$
$M^4$ = OH, SH, $BH_2$
M = O, S, NH, BH
FIG. 6

MASS MODIFYING FUNCTIONALITY R ( X SIMILAR TO FIG. 8 ):

H

Alkyl: $-(CH_2)_r-CH_3$ e.g. $-CH_3$, $-C_2H_5$,
and branched e.g. $-CH_3CH_2$)

$ICH_2(CH_2)_r-O-H$ 2,3-Epoxy-1-propanol $-(CH_2)_m-CH_2-O-H$ $-(CH_2)_m-CH_2-O-Alkyl$ $-(CH_2CH_2NH)_m-CH_2CH_2-NH_2$ $-[NH-(CH_2)_r-NH-\underset{O}{\overset{\|}{C}}-(CH_2)_r-\underset{O}{\overset{\|}{C}}-]_m-NH-(CH_2)_r-NH-\underset{O}{\overset{\|}{C}}-(CH_2)_r-\underset{O}{\overset{\|}{C}}-OH$ $-[NH(CH_2)_r-\underset{O}{\overset{\|}{C}}-]_m-NH-(CH_2)_r-\underset{O}{\overset{\|}{C}}-OH$ $-[NH-CHY-\underset{O}{\overset{\|}{C}}-]_m-NH-CHY-\underset{O}{\overset{\|}{C}}-OH$ $-[O-(CH_2)_r-\underset{O}{\overset{\|}{C}}-]_m-O-(CH_2)_r-\underset{O}{\overset{\|}{C}}-OH$ $-S-$ $-Si(Alkyl)_3$ $-Halogen$ $-N_3$ $-CH_2F$, $-CHF_2$, $-CF_3$ m = 0, 1-200 r = 1-20

FIG. 7

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear (ii) MOLECULE TYPE: other nucleic acid (iii) HYPOTHETICAL: YES (xi) SEQUENCE DESCRIPTION: SEQ ID NO:1:

GCCTTAGCTA                                                                                           10

(2) INFORMATION FOR SEQ ID NO:2:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: YES (xi) SEQUENCE DESCRIPTION: SEQ ID NO:2:

GCGGCCGCAG GTCA                                                                                      14

(2) INFORMATION FOR SEQ ID NO:3:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: YES (xi) SEQUENCE DESCRIPTION: SEQ ID NO:3:

AATTCAGCGG CCGC                                                                                      14

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: YES (xi) SEQUENCE DESCRIPTION: SEQ ID NO:4:

GGCCGCAGGT CA                                                                                        12

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO:5:

GGCCGCTGAA TT                                                                                        12

(2) INFORMATION FOR SEQ ID NO:6:

(i) SEQUENCE CHARACTERISTICS:

(A) LENGTH: 12 base pairs
(B) TYPE: nucleic acid
(C) STRANDEDNESS: single
(D) TOPOLOGY: linear (ii) MOLECULE TYPE: other nucleic acid (iii) HYPOTHETICAL: YES (xi) SEQUENCE DESCRIPTION: SEQ ID NO:6:

GGCCGCAGGT CA 12

(2) INFORMATION FOR SEQ ID NO:7:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: other nucleic acid (iii) HYPOTHETICAL: YES (xi) SEQUENCE DESCRIPTION: SEQ ID NO:7:

TTAAGTCGCC GG 12

(2) INFORMATION FOR SEQ ID NO:8:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: other nucleic acid (iii) HYPOTHETICAL: YES (xi) SEQUENCE DESCRIPTION: SEQ ID NO:8:

GCTAACTTGC 10

DNA SEQUENCING BY MASS SPECTROMETRY VIA EXONUCLEASE DEGRADATION

RELATED APPLICATIONS

This application is a File Wrapper Continuation (FWC) of U.S. Ser. No. 08/034,738 filed Mar. 19, 1993 (now abandoned).

BACKGROUND OF THE INVENTION

The fundamental role that determining DNA sequences has for the life sciences is evident. Its importance in the human genome project has been discussed and published widely [e.g. J. E. Bishop and M. Waldholz, 1991, Genome. The Story of the Most Astonishing Scientific Adventure of Our Time—The Attempt to Map All Genes in the Human Body. Simon & Schuster, New York].

The current state-of-the-art in DNA sequencing is summarized in recent review articles [e.g. B. Bartell, *The FASEB Journal*, 5, 40 (1991); G. L. Trainor, *Anal, Chem.* 62, 418 (1990), and references cited therein]. The most widely used DNA sequencing chemistry is the enzymatic chain termination method [F. Sanger et al., *Proc. Natl. Acad. Sci. USA*, 74, 5463 (1977)] which has been adopted for several different sequencing strategies. The sequencing reactions are either performed in solution with the use of different DNA polymerases, such as the thermophilic Taq DNA polymerase [M. A. Innes, *Proc. Natl. Acad, Sci. USA*, 85, 9436 (1988)] or specially modified T7 DNA polymerase ("SEQUENASE") [S. Tabor and C. C. Richardson, *Proc. Natl, Acad. Sci. USA*, 84, 4767 (1987)], or in conjunction with the use of polymer supports. See for example S. Stahl et al., *Nucleic Acids Res.*, 16, 3025 (1988); M. Uhlen, PCT Application WO 89/09282; Cocuzza et al., PCT Application WO 91/11533; and Jones et al., PCT Application WO 99/03575, incorporated by reference herein.

A central, but at the same time limiting, part of almost all sequencing strategies used today is the separation of the base-specifically terminated nested fragment families by polyacrylamide gel electrophoresis (PAGE). This method is time-consuming and error prone and can result in ambiguous sequence determinations. As a consequence of the use of PAGE, highly experienced personnel are often required for the interpretation of the sequence ladders obtained by PAGE in order to get reliable results. Automatic sequence readers very often are unable to handle artifacts such as "smiling", compressions, faint ghost bands, etc. This is true for the standard detection methods employing radioactive labeling such as $^{32}P$, $^{33}P$ or $^{35}S$, as well as for the so-called Automatic DNA Sequencers (e.g. Applied Biosystems, Millipore, DuPont, Pharmacia) using fluorescent dyes for the detection of the sequencing bands.

Apart from the time factor the biggest limitations of all methods involving PAGE as an integral part, however, is the generation of reliable sequence information, and the transformation of this information into a computer format to facilitate sophisticated analysis of the sequence data utilizing existing software and DNA sequence and protein data banks. With standard Sanger sequencing 200 to 500 bases of unconfirmed sequence information could be obtained in about 24 hours; with automatic DNA sequencers this number could be multiplied by approximately a factor of 10 to 20 due to processing several samples simultaneously. A further increase in throughput could be achieved by employing multiplex DNA sequencing [G. Church et al., *Science*, 240, 185–188 (1988); Köster et al., *Nucleic Acids Res. Symposium Ser. No,* 24, 318–21 (1991)] in which, by using a unique tag sequence, several sequencing ladders could be detected one after the other from the same PAGE after blotting, UV-crosslinking to a membrane, and hybridizations with specific complementary tag probes. However, this approach is still very laborious, often requires highly skilled personnel and can be hampered by the use of PAGE as a key element of the whole process.

A large scale sequencing project often starts with either a cDNA or genomic library of large DNA fragments inserted in suitable cloning vectors such as cosmid, plasmid (e.g. pUC), phagemid (e.g. pEMBL, pGEM) or single-stranded phage (e.g. M13) vectors [T. Maniatis, E. F. Fritsch and J. Sambrook (1982) Molecular Cloning. A Laboratory Manual. Cold Spring Harbor Laboratory, Cold Spring Harbor, N.Y.; *Methods in Enzymology*, Vol. 101 (1983), Recombinant DNA, Part C; Vol. 153 (1987), Recombinant DNA, Part D; Vol. 154 (1987), Recombinant DNA, Part E; Vol. 155 (1987), Recombinant DNA, Part F and Vol. 152 (1987), Guide to Molecular Cloning Techniques, Academic Press, New York]. Since large DNA fragments currently cannot be sequenced directly in one run because the Sanger sequencing chemistry allows only about 200 to 500 bases to be read at a time, the long DNA fragments have to be cut into shorter pieces which are separately sequenced. In one approach this is clone in a fully random manner by using, for example, unspecific DNAse I digestion, frequently cutting restriction enzymes, or sonification, and sorting by electrophoresis on agarose gels [*Methods in Enzymology, supra.*]. However, this method is time-consuming and often not economical as several sequences are sequenced many times until a contiguous DNA sequence is obtained. Very often the expenditure of work to close the gaps of the total sequence is enormous. Consequently, it is desirable to have a method which allows sequencing of a long DNA fragment in a non-random, i.e. direct, way from one end through to the other. Several strategies have been proposed to achieve this [*Methods of Enzymology, supra;* S. Henikoff, *Gene,* 28, 351–59 (1984); S. Henikoff, et al. U.S. Pat. No. 4,843,003; and PCT Application WO 91/12341]. However, none of the currently available sequencing methods provide an acceptable method of sequencing megabase DNA sequences in either a timely or economical manner. The main reason for this stems from the use of PAGE as a central and key element of the overall process.

In PAGE, under denaturing conditions the nested families of terminated DNA fragments are separated by the different mobilities of DNA chains of different length. A closer inspection, however, reveals that it is not the chain length alone which governs the mobility DNA chains by PAGE, but there is a significant influence of base composition on the mobility [R. Frank and H. Köister, *Nucleic Acids Res.,* 6, 2069 (1979)]. PAGE therefore is not only a very slow, but also an unreliable method for the determination of molecular weights, as DNA fragments of the same length but different sequence/base composition could have different mobilities. Likewise, DNA sequences which have the same mobility could have different sequence/base compositions.

The most reliable way for the determination of the sequence/base composition of a given DNA fragment would therefore be to correlate the sequence with its molecular weight. Mass spectrometry is capable of doing this. The enormous advantage of mass spectrometry compared to the above mentioned methods is the speed, which is in the range of seconds per analysis, and the accuracy of mass determination, as well as the possibility to directly read the collected mass data into a computer. The application of mass spectrometry for DNA sequencing has been investigated by several groups [e.g. *Methods in Enzymology*, Vol. 193: Mass Spectrometry, (J. A. McCloskey, editor), 1990, Academic Press, New York; K. H. Schramm *Biomedical Applications of Mass Spectrometry*, 34, 203–287 (1990); P. F. Crain *Mass Spectrometry Reviews*, 9, 505 (1990)].

Most of the attempts to use mass spectrometry to sequence DNA have used stable isotopes for base-specific labeling, as for instance the four sulfur isotopes $^{32}S$, $^{33}S$, $^{34}S$ and $^{36}S$. See, for example, Brennan et al., PCT Application WO 89/12694, R. L. Mills U.S. Pat. No. 5,064,754, U.S. Pat. No. 5,002,868, Jacobson et al.; Hean European Patent Application No. A1 0360676. Most of these methods employ the Sanger sequencing chemistry and—which jeopardizes to some extent the advantages of mass spectrometry—polyacrylamide gel electrophoresis with some variations such as capillary zone electrophoresis (CZE) to separate the nested terminated DNA fragments prior to mass spectrometric analysis.

One advantage of PAGE is the property of being a parallel method, i.e. several samples could be analyzed simultaneously (though this is not true for CZE which is a serial method), whereas mass spectrometry allows, in general, only a serial handling of the samples. In a U.S. patent application No. 08/001,323, mass spectrometric DNA sequencing is proposed without the use of PAGE, employing desorption/ionization techniques applicable to larger biopolymers such as electrospray (ES) [J. B. Fenn et al., *J. Phys. Chem.*, 88, 4451–59 (1984) and Fenn et al., PCT Application No. WO 90/14148 and B. Ardrey, *Spectroscopy Europe*, 4, 10–18 (1992)] and matrix assisted laser desorption/ionization (MALDI) mass spectrometry [F. Hillenkamp et al., Laser Desorption Mass Spectrometry, Part I: Mechanisms and Techniques and Part II: Performance and Application of MALDI of Large Biomolecules, in *Mass Spectrometry in the Biological Science: A Tutorial* (M. L. Gross, editor), 165–197 (1992), Kluwer Academic Publishers, The Netherlands] which can facilitate determination of DNA sequences by direct measurement of the molecular masses in the mixture of base-specifically terminated nested DNA fragments. By integrating the concept of multiplexing through the use of mass-modified nucleoside triphosphate derivatives, the serial mode of analysis typical for current mass spectrometric methods can be changed to a parallel mode [H. Köster, U.S. patent application No. 08/001,323, supra].

MALDI and ES mass spectrometry are in some aspects complementary techniques. While ES, using an atmospheric pressure ionization interface (API), can accommodate continuous flow streams from high-performance liquid chromatoghraphs (HPLC) [K. B. Tomer, et al. *Biological Mass Spectrometry*, 20, 783–88 (1991)] and capillary zone electrophoresis (CZE) [R. D. Smith et al., *Anal. Chem.*, 60, 436–41 (1988)] this is currently not available for MALDI mass spectrometry. On the other hand, MALDI mass spectrometry is less sensitive towards buffer salts and other low molecular weight components in the analysis of larger molecules with a TOF mass analyzer [Hillenkamp et al. (1992), supra]; in contrast ES is very sensitive towards by-products of low volatility. While the high mass range in ES mass spectrometry is accessible through the formation of multiply charged molecular ions, this is achieved in MALDI mass spectrometry by applying a time-of-flight (TOF) mass analyzer and the assistance of an appropriate matrix to volatilize the biomolecules. Similar to ES, a thermospray interface has been used to couple HPLC on-line with a mass analyzer. Nucleosides originating from enzymatic hydrolysates have been analyzed using such a configuration [C. G. Edmonds et al. *Nucleic Acids Res.*, 13, 8197–8206 (1985)]. However, Edmonds et al. does not disclose a method for nucleic acid sequencing.

A complementary and completely different approach to determine the DNA sequence of a long DNA fragment would be to progressively degrade the DNA strand using exonucleases from one side—nucleotide by nucleotide. This method has been proposed by Jett et al. See J. H. Jett et al. *J. Biomolecular Structure & Dynamics*, 7, 301–309 (1989); and J. H. Jett et al. PCT Application No. WO 89/03432. A single molecule of a DNA or RNA fragment is suspended in a moving flow stream and contacted with an exonuclease which cleaves off one nucleotide after the other. Detection of the released nucleotides is accomplished by specifically labeling the four nucleotides with four different fluorescent dyes and involving laser induced flow cytometric techniques.

However strategies which use a stepwise enzymatic degradation process can suffer from the problem that this process is difficult to synchronize, i.e. the enzymatic reaction soon comes out of phase. Jett et al., supra, have attempted to address this problem by degrading just one single DNA or RNA molecule by an exonuclease. However, this approach is very hard, as handling a single molecule, keeping it in a moving flow stream, and achieving a sensitivity of detection which clearly identifies one single nucleotide are only some of the very difficult technical problems to be solved. In addition, in using fluorescent tags, the physical detection process for a fluorescent signal involves a time factor difficult to control and the necessity to employ excitation by lasers can cause photo-bleaching of the fluorescent signal.

The invention described here addresses most of the problems described above inherent to currently existing DNA sequencing processes and provides chemistries and systems suitable for high-speed DNA sequencing a prerequisite to tackle the human genome (and other genome) sequencing projects.

SUMMARY OF THE INVENTION

In contrast to most sequencing strategies, the process of this invention does not use the Sanger sequencing chemistry, polyacrylamide gel electrophoresis or radioactive, fluorescent or chemiluminescent detection. Instead the process of the invention adopts a direct sequencing approach, beginning with large DNA fragments cloned into conventional cloning vectors, and based on mass spectrometric detection. To achieve this, the DNA is by means of protection, specificity of enzymatic activity, or immobilization, unilaterally degraded in a stepwise manner via exonuclease digestion and the nucleotides or derivatives detected by mass spectrometry.

Prior to this enzymatic degradation, sets of ordered deletions can be created which span the whole sequence of the cloned DNA fragment. In this manner, mass-modified nucleotides can be incorporated using a combination of exonuclease and DNA/RNA polymerase. This enables either multiplex mass spectrometric detection, or modulation of the activity of the exonuclease so as to synchronize the degradative process. In another embodiment of the invention the phasing problem can be resolved by continuously applying small quantities of the enzymatic reaction mixture onto a moving belt with adjustable speed for mass spectrometric detection. In yet another embodiment of the invention, the throughput could be further increased by applying reaction mixtures from different reactors simultaneously onto the moving belt. In this case the different sets of sequencing reactions can be identified by specific mass-modifying labels attached to the four nucleotides. Two-dimensional multiplexing can further increase the throughput of exonuclease mediated mass spectrometric sequencing as being described in this invention.

BRIEF DESCRIPTION OF THE DRAWINGS

The accompanying drawings form a part of the specifications and serve the purpose of providing examples illustrating certain embodiments of the present invention. Together with the description they help to explain the principles of the invention without limiting the scope of it.

FIG. 6 illustrates various structures of modified nucleoside triphosphates useful for the enzymatic incorporation of mass-modified nucleotides into the DNA or RNA to be sequenced.

FIG. 7 shows some possible functional groups (R) useful to either mass-modification of nucleotides in discrete increments for differentiation by mass spectrometry and/or to modulate the enzymatic activity of an exonuclease.

DETAILED DESCRIPTION OF THE INVENTION

Figure 1:
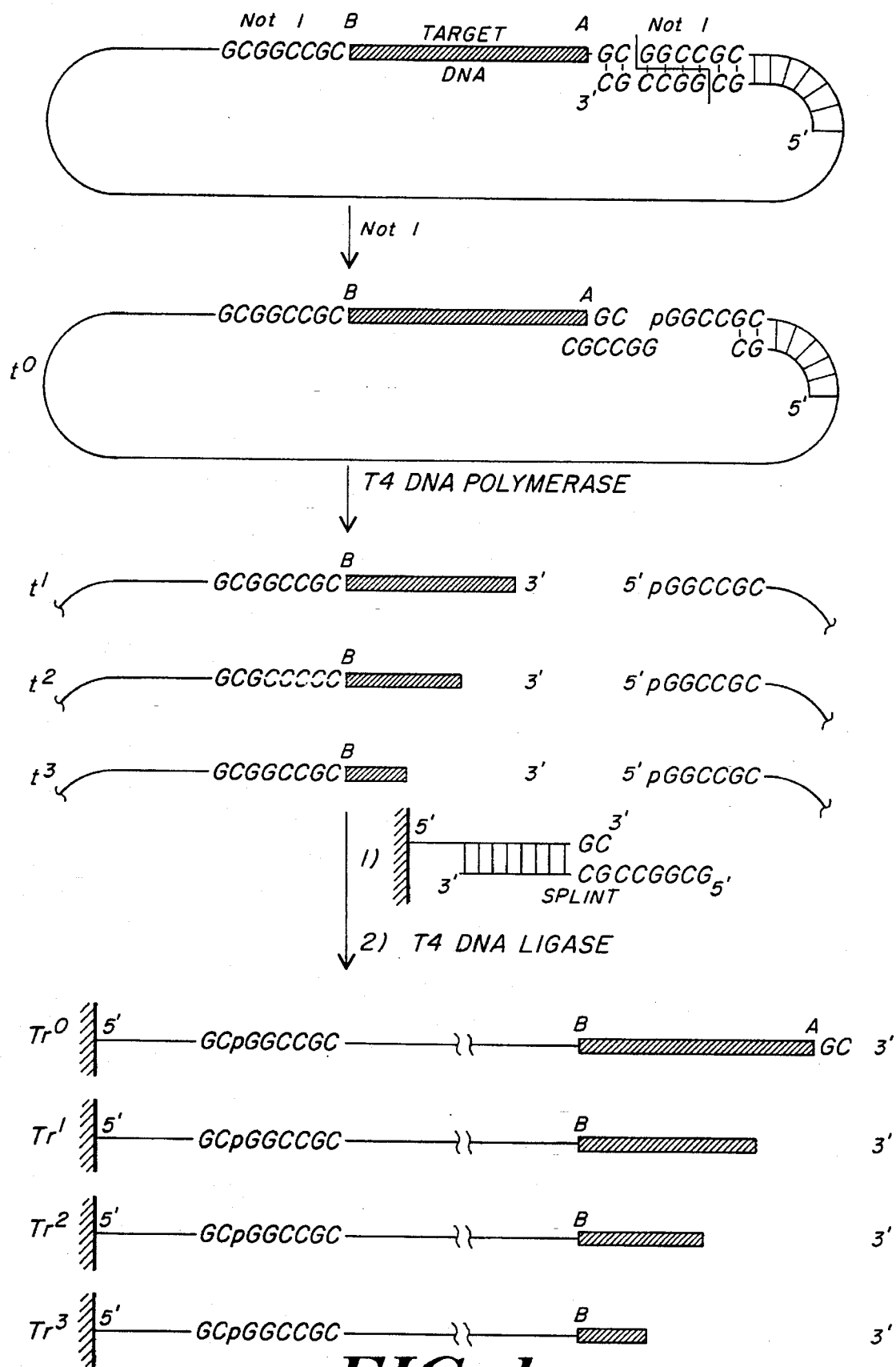
FIG. 1 illustrates a process of exonuclease sequencing beginning with a single-stranded nucleic acid.

The starting point for the process of the invention can be, for example, DNA cloned from either a genomic or cDNA library, or a piece of DNA isolated and amplified by polymerase chain reaction (PCR) which contains a DNA fragment of unknown sequence. Libraries can be obtained, for instance, by following standard procedures and cloning vectors [Maniartis, Fritseh and Sambrook (1982), supra; *Methods in Enzymology*, Vol. 101 (1983) and Vol. 152–155 (1987), supra]. Appropriate cloning vectors are also commercially available. As will be apparent, the invention is not limited to the use of any specific vector constructs and cloning procedures, but can be applied to any given DNA fragment whether obtained, for instance, by cloning in any vector or by the Polymerase Chain Reaction (PCR). The unknown DNA sequence can be obtained in either double-stranded form using standard PCR or in a single-stranded form employing asymmetric PCR [*PCR Technology*: Principles and Applications for DNA Amplification (Erlich, editor), M. Stockton Press, New York (1989)].

For those skilled in the art it is dear that both DNA and RNA can be exonucleolytically degraded from either the 5' or 3' end depending upon the choice of exonuelease. Similarly the sequence of an unknown DNA molecule can be determined directly by exonuelease digestion, or alternatively, the DNA fragment of unknown sequence can be transcribed first into a complementary RNA copy which is subsequently exonucleolytically degraded to provide the RNA sequence. Appropriate vectors, such as the pGEM (Promega) vectors, are useful in the present as they have specific promoters for either the SP6 or T7 DNA dependent RNA polymerases flanking the multiple cloning site. This feature allows transcription of both unknown DNA strands into complementary RNA for subsequent exonuclease sequencing. Furthermore, these vectors, belonging to the class of phagemid vectors, provide means to generate single stranded DNA of the unknown double stranded DNA. Thus, by using two vectors which differ only in the orientation of the fi origin of replication, both strands of the unknown DNA sequence can be obtained in a single stranded form and utilized for subsequent exonuclease sequencing. The scope of the invention is also not limited by the choice of restriction sites. There is, however, a preference for rare cutting restriction sites to keep the unknown DNA fragment unfragmented during the manipulations in preparation for exonuclase sequencing. The following description and the FIGURES do serve the purpose by way of examples to illustrate the principles of the invention. Variations which are within the scope of the invention will be obvious to those skilled in the art. Various mass spectrometric configurations are within the scope of the invention: For desorption/ionization e.g. fast atomic bombardment (FAB), plasma desorption (PD), thermospray (TS) and preferentially electrospray (ES) and laser desorption with and without an appropriate matrix (LD or MALDI); as mass analyzer e.g. a time-of-flight (TOF) configuration or a quadrupole is applicable.

(i) Preparation of unknown nucleic acid sequence for exonuclease sequencing:

FIG. 1 describes the process for a single stranded DNA insert ("Target DNA") of a single stranded circular cloning vector. The boundaries of the target DNA are designated A and B. The target DNA, as illustrated in FIG. 1, has been cloned into the Not I site of a vector. A synthetic oligodeoxynucleotide [N. D. Sinha, J. Biernat, J. McManus and H. Köster, *Nucleic Acids Res.*, 12, 4539 (1984)] which will restore the Not I site to double-strandedness and which is complementary to the vector sequence flanking the A boundary of the insert DNA is hybridized to that site and cleaved by Not I restriction endonuclease. The two pieces of the synthetic oligodeoxynucleotide can then be removed by molecular sieving, membrane filtration, precipitation, or other standard procedures.

FIG. 1 also illustrates a set of ordered deletions ($t^0, t^1, t^2, t^3$) which can be obtained by the time-limited action of an exonuclease, e.g. T4 DNA polymerase, in the absence of dNTPs. The set of deletions can be immobilized on a solid support Tr ($Tr^0, Tr^1, Tr^2, Tr^3$), or alternatively, the set of ordered deletions can be obtained in a heterogeneous reaction by treating the solid support $Tr^0$ containing the complete target DNA sequence with an exonuclease in a time-limited manner. In the instance where the 3' termini of each time point are too heterogeneous (i.e. "fuzzy") to be analyzed directly by exonuclease mediated mass spectrometric sequencing, circularization of the template and a cloning step can be performed prior to this sequencing process with single transformed colonies selected.

Figure 9:
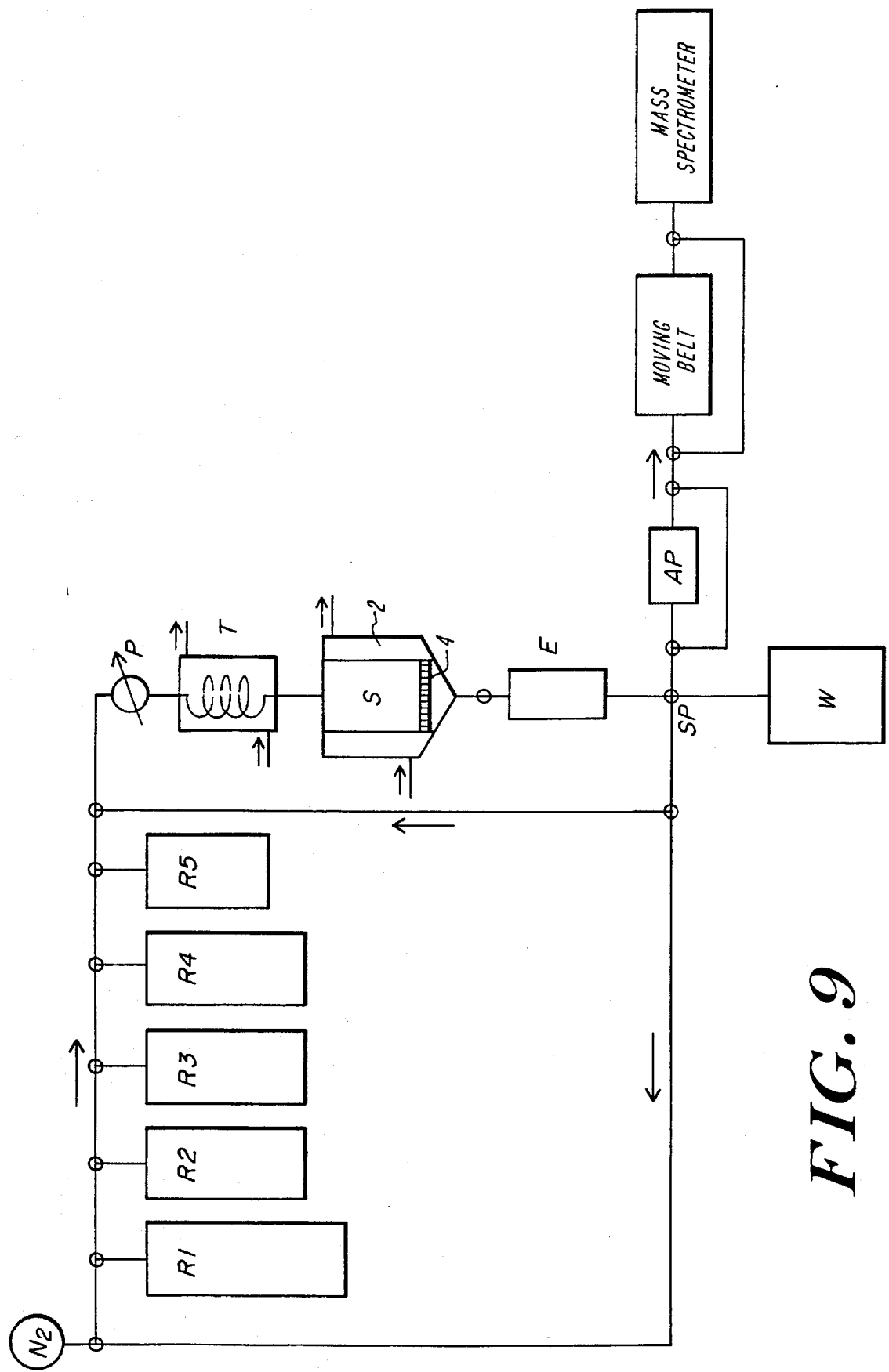
FIG. 9 is a schematic drawing of a sequencing reactor system.

A single stranded linear DNA fragment carrying the unknown sequence with its A boundary at the 3' end can be directly sequenced by an 3' exonuclease in an apparatus described below and schematically depicted in FIG. 9, provided that the exonuclease is immobilized within the reactor on, for example, beads, on a frit, on a membrane located on top of the frit or on the glass walls of a capillary or entrapped in a gel matrix or simply by a semipermeable membrane which keeps the exonuclease in the reactor while the linear DNA fragment is circulating through a loop.

At time intervals, or alternatively as a continuous stream, the reaction mixture containing the buffer and the released nucleotides is fed to the mass spectrometer for mass determination and nucleotide identification. In another embodiment, the stream containing the nucleotides released by exonuclease action can be passed through a second reactor or series of reactors which cause the released nucleotide to be modified. For example, the second reactor can contain an immobilized alkaline phosphatase and the nucleotides passing therethrough are transformed to nucleosides prior to feeding into the mass spectrometer. Other mass-modifications are described below.

In general, when it is the released nucleotide (or ribonucleotide) which is mass-modified, the modification should take as few steps as possible and be relatively efficient. For example, reactions used in adding base protecting groups for oligonucleotide synthesis can also be used to modify the released nucleotide just prior to mass spectrometric analysis. For instance, the amino function of adenine, guanine or cytosine can be modified by acylation. The amino acyl function can be, by way of illustration, an acetyl, benzoyl, isobutyryl or anisoyl group. Benzoylchloride, in the presence of pyridine, can acylate the adenine amino group, as well as the deoxyribose (or ribose) hydroxyl groups. As the glycosidic linkage is more susceptible to hydrolysis, the sugar moiety can be selectively deacylated if the acyl reaction was not efficient at those sites (i.e. heterogeneity in molecular weight arising from incomplete acylation of the sugar). The sugar moiety itself can be the target of the mass-modifying chemistry. For example, the sugar moieties can be acylated, tritylated, monomethoxytritylated, etc. Other chemistries for mass-modifying the released nucleotides (or ribonucleotides) will be apparent to those skilled in the art.

In another embodiment the linear single stranded DNA fragment can be anchored to a solid support. This can be achieved, for example, by covalent attachment to a functional group on the solid support, such as through a specific oligonucleotide sequence which involves a spacer of sufficient length for the ligase to react and which is covalently attached via its 5' end to the support (FIG. 1). A splint oligonucleotide with a sequence complementary in part to the solid bound oligonucleotide and to the 5' end of the linearized single stranded vector DNA allows covalent attachment of the DNA to be sequenced to the solid support. After annealing, ligation (i.e. with T4 DNA ligase) covalently links the solid bound oligonucleotide and the DNA to be sequenced. The splint oligonucleotide can be subsequently removed by a temperature jump and/or NaOH treatment, or washed off the support using other standard procedures. The solid support with the linear DNA sample is transferred to the reactor (FIG. 9) and contacted with an exonuclease in solution. As illustrated, where the 3' end of the unknown DNA fragment is exposed (ie unprotected), a 3' exonuclease is employed. The released nucleotides, or modified nucleotides if intermediately contacted with a modifying agent such as alkaline phosphatase, are identified by mass spectrometry as described above. Other linking groups are described herein, and still others will be apparent to those skilled in the art from the invention described here.

The solid supports can be of a variety of materials and shapes, such as beads of silica gel, controlled pore glass, cellulose, polyacrylamide, sepharose, sephadex, agarose, polystyrene and other polymers, or membranes of polyethylene, polyvinylidendifluoride (PVDF) and the like. The solid supports can also be capillaries, as well as frits from glass or polymers. Various 3' exonucleases can be used, such as phosphodiesterase from snake venom, Exonuclease VII from *E. coli,* Bal 31 exonuclease and the 3'–5' exonuclease activity of some DNA polymerases exerted in the absence of dNTPs, as for example T4 DNA polymerase.

In using a phagemid vector with an inverted f1 origin of replication, the B boundary would be located at the 3' end of the immobilized linear single stranded DNA and exposed to exonuclease sequencing using the same restriction endonuclease, hybridizing oligodeoxynucleotide and splint oligonucleotide. As another embodiment of this invention, the hybridizing oligonucleotide can also be designed to bind a promoter site upstream of the A boundary and by doing so restoring the doublestranded promoter DNA. Directly, or with a short initiator oligonucleotide carrying an attachment functionality at the 5' end, transcription can be initiated with the appropriate specific DNA dependent RNA polymerase [*Methods in Enzymology,* Vol. 185, Gene Expression Technology (1990); J. F. Milligan, D. R. Groebe, G. W. Witherell and O. C. Uhlenbeck, *Nucleic Acids Res.,* 15, 8783–98 (1987); C. Pitulle, R. G. Kleineidam, B. Sproat and G. Krupp, *Gene,* 112, 101–105 (1992) and H. Köster U.S. patent application No. 08/001,323, supra]. The RNA transcript can be transferred to the reactor (FIG. 9) and contacted with an immobilized or otherwise contained exonuclease, or immobilized via the 5' functionality of the initiator oligonucleotide incorporated in the RNA transcript to a solid support and then contacted with an exonuclease in solution.

Depending on the length of the DNA insert (i.e. number of nucleotides between boundary A and B in FIG. 1) the mass spectrometric exonuclease sequencing process can allow the complete sequence from A to B to be determined in one run. Alternatively, prior to exonuclease sequencing, a set of ordered deletions can be prepared according to standard procedures [e.g. *Methods in Enzymology,* Vol. 101 (1983) and Vol. 152–155 (1987); R. M. K. Dale et al., *Plasmid,* 13, 31–40 (1985)], such that, in FIG. 1 the steps $Tr^0$ to $Tr^3$ can represent either different time values of the mass spectrometric exonuclease sequencing reaction from immobilized DNA fragments or different starting points for the exonuclease DNA/RNA mass spectrometric sequencing process. In either case the principle of the invention described provides a process by which the total sequence of the insert can be determined.

Figure 2:
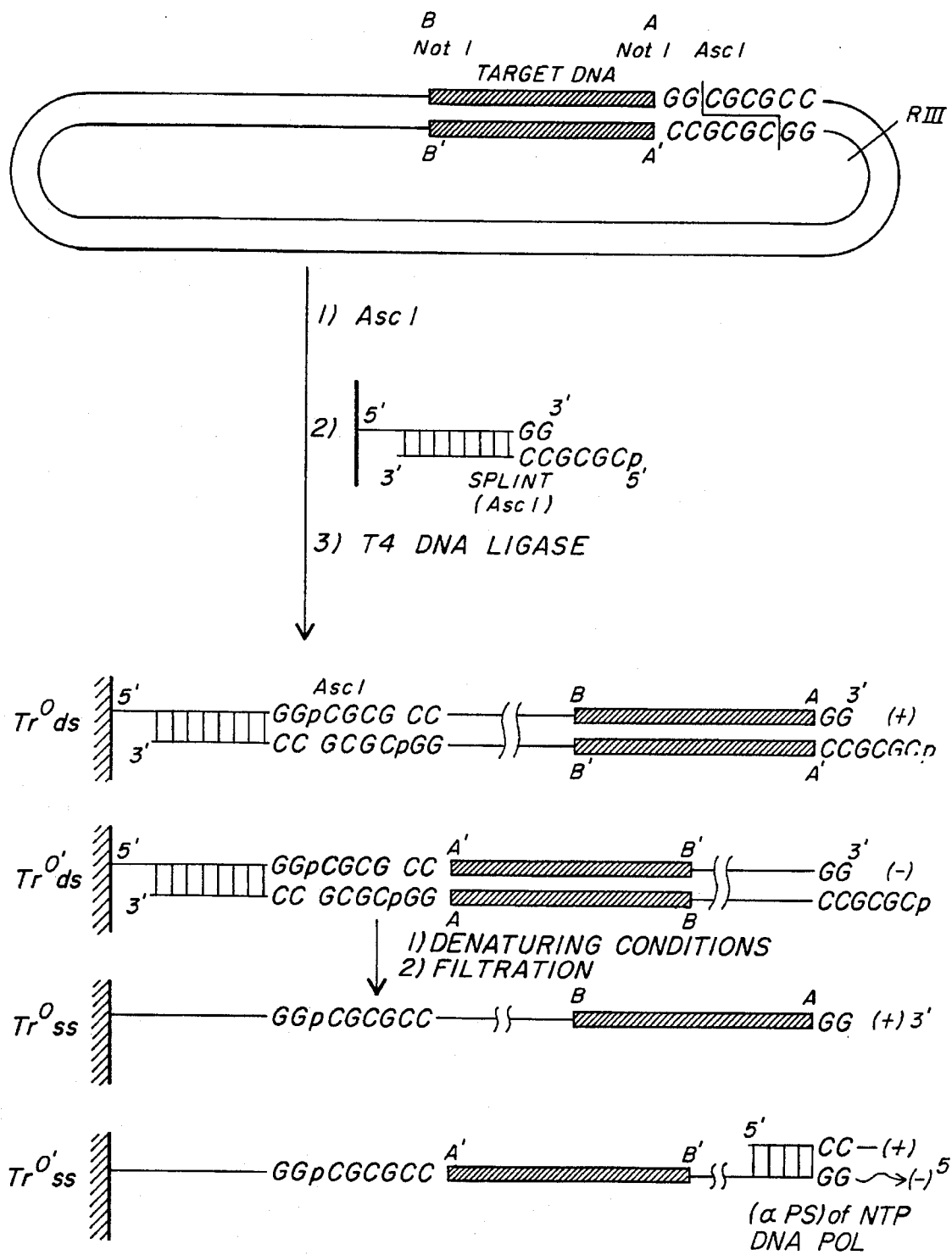
FIG. 2 illustrates a process similar to FIG. 1, however, starting with a target nucleic acid inserted into a double-stranded vector.

In another embodiment of the invention the unknown DNA sequence (target DNA) is inserted into a double-stranded cloning vector (FIG. 2) or obtained in double-stranded form, as for example by a PCR (polymerase chain reaction) process [*PCR Technology*, (1989) supra]. The DNA to be sequenced is inserted into a cloning vector, such as ligated into the Not I site as illustrated in FIG. 2. Adjacent to the A boundary there can be located another cutting restriction endonuclease site, such as an Asc I endonuclease cleavage site. The double-stranded circular molecule can be linearized by treatment with Asc I endonuclease and ligated to a solid support using a splint oligodeoxynucleotide (and ligase) as described above which restores the Asc I restriction site ($Tr^0ds$ and $Tr^{0'}ds$). The strand which is not immobilized can be removed by subjecting the double stranded DNA to standard denaturing conditions and washing, thereby generating single-stranded DNAs immobilized to the solid support ($Tr^0ss$ and $Tr^{0'}ss$). Since the unknown double-stranded DNA sequence can be ligated in either orientation to the support there can exist two non-identical 3' termini (+ and − strand) immobilized, which can result in ambiguous sequencing data. The immobilized fragment which carries the vector DNA sequence at the 3' end ($Tr^{0'}ss$) can be protected from 3' exonuclease degradation during the sequencing process by, for example, annealing with an oligodeoxynucleotide complementary to the 3' end of the strand to be protected. As there can only be hybridization at one 3' terminus, i.e. to the wrong single-stranded DNA with (−) strand information ($Tr^{0'}ss$), some alpha-thio dNTP's can be incorporated into the immobilized (−) strand via treatment with a DNA polymerase and completely protect that strand from exonucleolytic degradation [P. M. J. Burgers and F. Eckstein, *Biochemistry*, 18, 592 (1979); S. Labeit, H. Lehrach and R. S. Goody, *DNA*, 5, 173 (1986); S. Labeit, H. Lehrach and R. S. Goody in *Methods in Enzymology*, Vol. 155, page 166 (1987), supra]. If desired, after incorporation of exonuclease resistant nucleotides, the oligonucleotide primer may be removed by a washing step under standard denaturing conditions. The immobilized single-stranded DNAs are transferred to the sequencing reactor (FIG. 9) and the sample with the unknown sequence at the 3' end is degraded by an exonuclease in a stepwise manner. The liberated nucleotides, or optionally modified nucleotides, are continuously fed into the mass spectrometer to elucidate the sequence.

As above, where the inserted DNA is too long for determining the complete sequence information between the boundaries A and B (FIG. 2) in one run of exonuclease mass spectrometric sequencing, a series of overlapping ordered deletions can be constructed according to standard procedures, e.g. utilizing the restriction site RIII producing 3' sticky ends inert towards exonuclease III digestion [*Methods in Enzymology*, Vol 152–155 (1987) and S. Henikoff, *Gene*, (1984), supra]. When required, the deletion mutants can be recircularized and used to transform host cells following standard procedures. Single colonies of the transformed host cells are selected, further proliferated, and the deletion mutant isolated and immobilized as single-stranded DNAs, similar to the process described above and subsequently analyzed by exonuclease mass spectrometric sequencing. Alternatively, the immobilized full length single stranded DNA ($Tr^0ss$) can be treated in time-limited reactions with an exonuclease such as T4 DNA polymerase in the absence of NTPs, to create a set of immobilized ordered deletions for subsequent exonuclease mass spectrometric sequencing. However, in case the 3' termini are too heterogeneous for direct mass spectrometric exonuclease sequencing an intermediate cloning step can be included. In yet another embodiment, the exonuclease mediated sequencing can be performed by providing the single-stranded (ss) nucleic acid fragment in solution. This can be achieved by treating the solid support, e.g. $Tr^0ss$, with an oligonucleotide complementary to the unique Asc I site. After hybridization this site is now double-stranded (ds) and susceptible to Asc I endonuclease cleavage and release of the single-stranded fragment.

If a cloning vector such as one of the pGEM family (Promega Corp.) is used, both strands of the double-stranded target DNA can be transcribed separately dependent upon which of the specific promoters flanking the insertion site is used (located next to the A or B boundary of the insert, FIG. 2) and the corresponding specific DNA dependent RNA polymerase (i.e. SP6 or T7 RNA polymerase). These RNA transcripts can be directly transferred to the sequencing reactor (FIG. 9) for mass spectrometric exonuclease sequencing using an immobilized or entrapped exonuclease. In an alternate embodiment, the transcription process is initiated via initiator oligonucleotides with a 5' functionality allowing the subsequent immobilization of the RNA transcripts to a solid support [H. Köster, U.S. patent application No. 08/001,323, supra]; in this case the mass spectrometric sequencing can be performed within the sequencing reactor using an exonuclease in solution. The stepwise liberated ribonucleotides, or modified ribonucleotides (i.e. ribonucleosides generated by passing through a reactor containing immobilized alkaline phosphatase), are fed to the mass spectrometer for sequence determination.

(ii) Introduction of mass-modified nucleotides for multiplex exonuclease sequencing:

Since standard mass spectrometry is a serial process, the throughput can be limited. However, in the present invention the throughput can be considerably increased by the introduction of mass-modified nucleotides into the DNA or RNA to be sequenced allowing for a parallel analysis of several nucleic acid sequences simultaneously by mass spectrometry. See H. Köster, U.S. patent application No. 08/001,323, supra. Low molecular weight nucleic acid components, such as unmodified or mass modified nucleotides/nucleosides, can be analyzed simultaneously by multiplex mass spectrometry.

Figure 3:
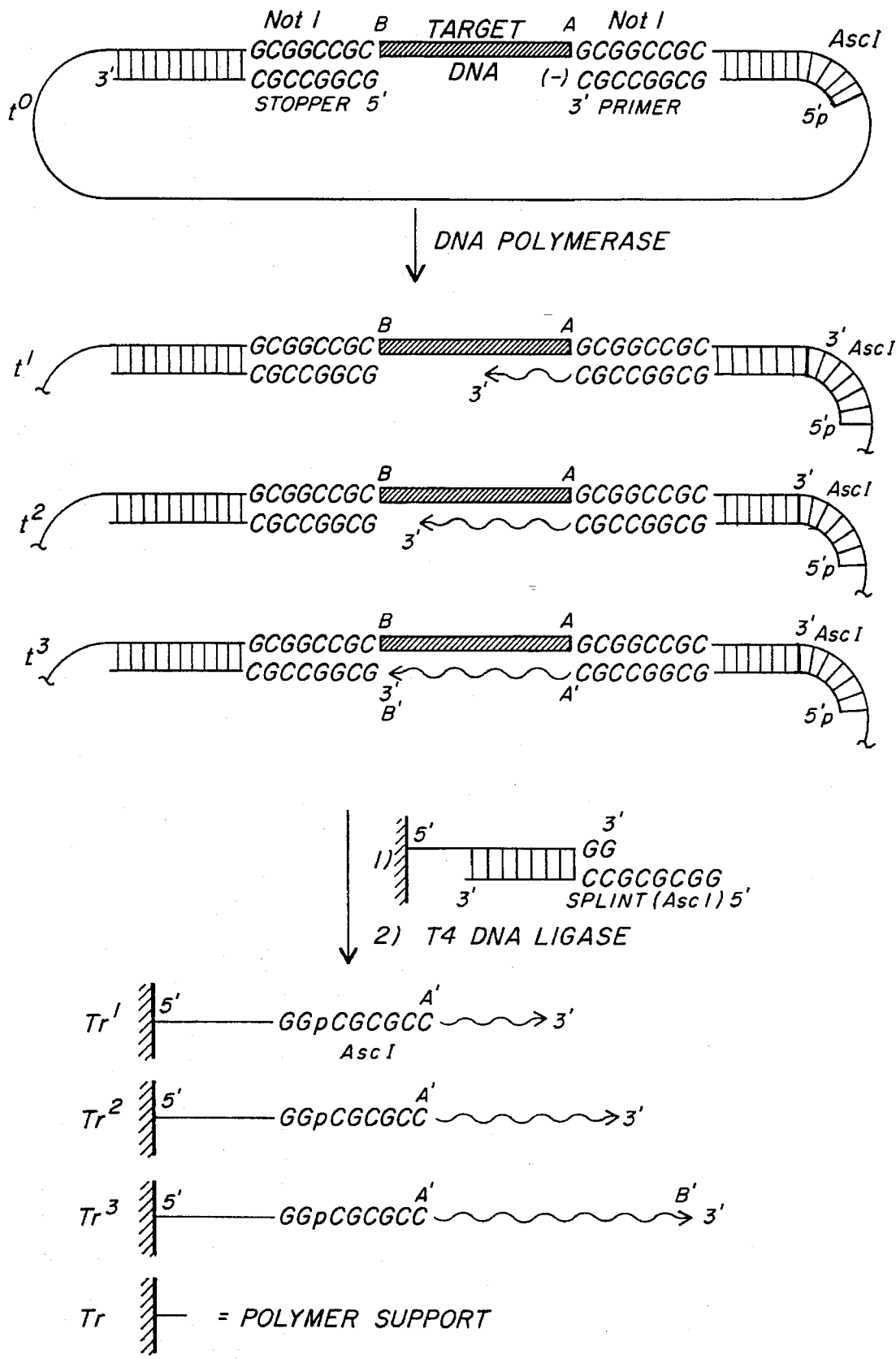
FIG. 3 illustrates a method for introducing mass-modified nucleotides into a target nucleic acid sequence multiplexing mass spectrometry.

Mass-modified nucleotides can be incorporated by way of mass modified nucleoside triphosphates precursors using various methods. For example, one can begin with the insert of the target DNA sequence in a single-stranded cloning vector by having a "primer" and a "stopper" oligonucleotide bound to the complementary vector sequences located at the A and B boundary of the insert DNA respectively (FIG. 3) and a template directed DNA polymerase, preferentially one lacking the 3'-5' and 5'-3' exonuclease activity such as Sequenase, version 2.0 (US Biochemicals, derived from T7 DNA polymerase), Taq DNA polymerase or AMV reverse transcriptase. In the illustrative embodiment, the unknown DNA sequence has been inserted in a restriction endonuclease site such as Not I. Adjacent to the A boundary another restriction endonuclease site, such as the Asc I site, can be located within the primer binding site such that the partly double-stranded circular DNA can be cleaved at the unique Asc I site and the mass-modified (−) strand ($t^3$ in FIG. 3) isolated by standard procedures (i.e. membrane filtration, molecular sieving, PAGE or agarose gel electrophoresis)

and, if desired, coupled to a solid support via a splint oligonucleotide restoring the Asc I site in double-stranded form for ligation by T4 DNA ligase (FIG. 3). After having removed the splint oligonucleotide the immobilized single-stranded DNA fragment with its B' boundary at the 3' end (i.e. Tr$^3$) is ready for exonuclease mediated mass spectrometric sequencing. In another illustrative embodiment, the same primer can be used even when the vector has no complementary Asc I site. Although the primer will not hybridize with its 5' terminal sequence to the vector as is shown in FIG. 3, it will nevertheless allow the covalent attachment of the single-stranded mass-modified DNA to the solid support using the same splint oligonucleotide as described above. In yet another embodiment the primer can carry a non-restriction site sequence information at its 5' end, which may or may not be complementary to the opposite vector sequence, but is complementary to a specific splint oligodeoxynucleotide which allows the covalent attachment to the solid support. The latter two procedures do not require cleavage with a restriction endonuclease and separation of the strands. The reaction mixture obtained after enzymatic synthesis of the mass-modified (−)strand can be directly joined to the solid support and the circular vector DNA and the stopper oligonucleotide can be removed under denaturing conditions. In yet another embodiment, the generation of a set of ordered deletions of the target DNA sequence information and the incorporation of mass modified nucleotides can be combined by terminating the DNA polymerase reaction at different time intervals (i.e. t$^0$, t$^1$, t$^2$, t$^3$, FIG. 3) to generate a ladder of mass-modified (−) strands. In case the 3' termini of each time point are too heterogeneous for mass spectrometric exonuclease sequencing a circularization and cloning step as described above can be included.

Figure 14:
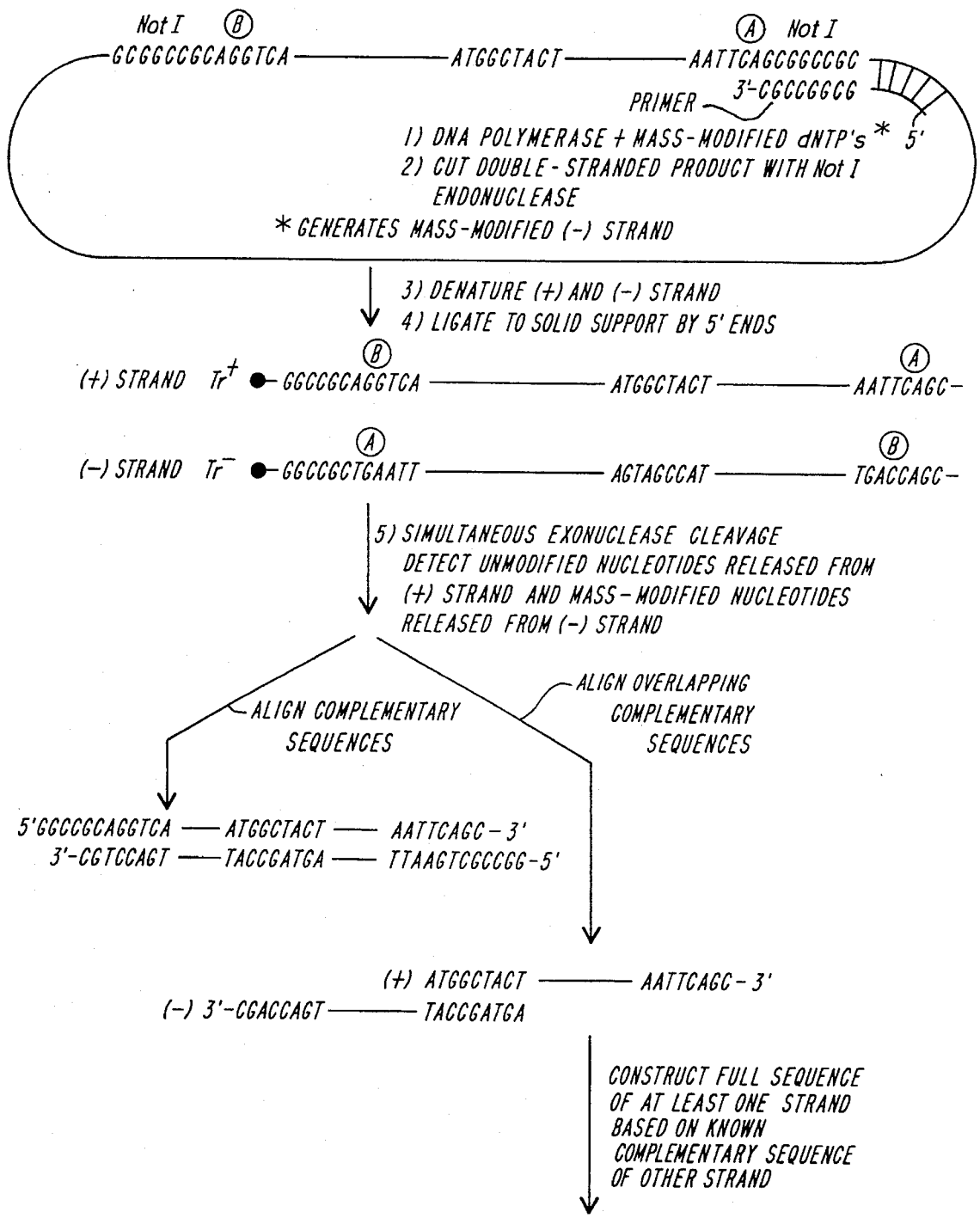
FIG. 14 illustrates a method for double-stranded exonuclease sequencing for mass spectrometric sequence determination.

As illustrated in FIG. 14, both the (+) and (−) strand can be exonuclease sequenced simultaneously. Incorporation of mass-modified nucleotides into one of the (+) or (−) strands can be carried out as described above. In the illustrative embodiment, both the (+) and (−) strands are ligated to solid supports and exonucleased simultaneously. The presence of the mass-modified nucleotides in the (−) strand can allow for differentiation of mass spectrometric signals arising from nucleotides released from both strands. Where exonuclease sequencing can proceed essentially between the A and B boundaries in one pass, the sequence of the (−) strand can be inverted and aligned with the complementary sequence. An advantage to this approach is the identification of ambiguous sequencing data (i.e. base pair mismatches arising from error of sequencing one of the strands). Alternatively, the full sequence can be obtained from partial exonuclease sequencing of both the (+) and (−) strands provided that sequencing proceeds to an overlapping point on each strand. By searching for the complementary overlapping region of each sequence fragment and aligning the two sequence fragments, the sequence of the remainder of one or both of the strands can be "reconstructed" based on the known sequence of the other. This later example provides a means of sequencing in "one pass" a much larger DNA fragment than would be possible by exonuclease sequencing only one strand.

In using vectors of the phagemid type (e.g. pGEM family, Promega Corp.) both strands of the unknown DNA fragment can be mass-modified by using just the vector which carries the f1 origin of replication in the opposite direction.

As further embodiments of this invention and in analogy to the reactions described above, RNA transcripts of both strands can be obtained utilizing, for example, transcription promoter regions flanking the insertion site, restoring the double-stranded promoter site by complementary oligonucleotides [*Methods in Enzymology*, Vol. 185, (1990); Uhlenbeck et al., *Nucleic Acids Res.*, (1987), supra] and transcribing with appropriate RNA polymerases in the presence of mass-modified ribonucleoside triphosphates. As above, the mass-modified RNA can be directly transferred to the sequencing reactor for mass spectrometric sequencing using an immobilized or entrapped exonuclease. In another embodiment the transcription can be initiated with initiator oligonucleotides [Krupp et al., *Gene*, (1992), supra] carrying a 5' functionality for subsequent attachment of the mass-modified RNAs to a solid support. In the later instance, the immobilized mass-modified RNAs can be contacted in the sequencing reactor (FIG. 9) with an exonuclease in solution for mass spectrometric sequencing.

Figure 4A:
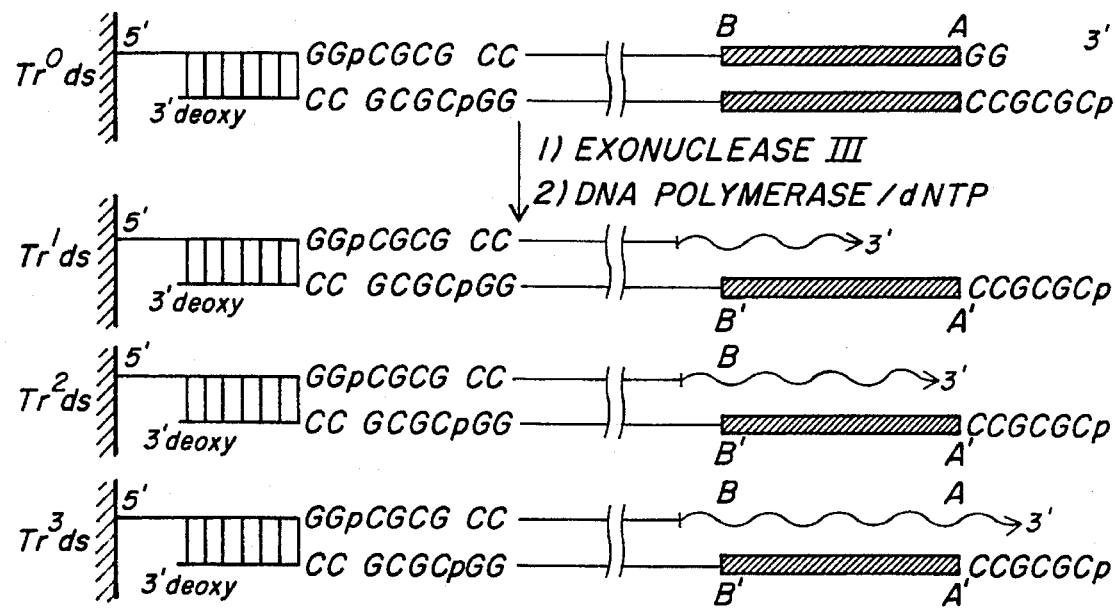
FIG. 4A and 4B illustrate methods for introducing mass-modified nucleotides into a target nucleic acid sequence multiplexing mass spectrometry.
Figure 4B:
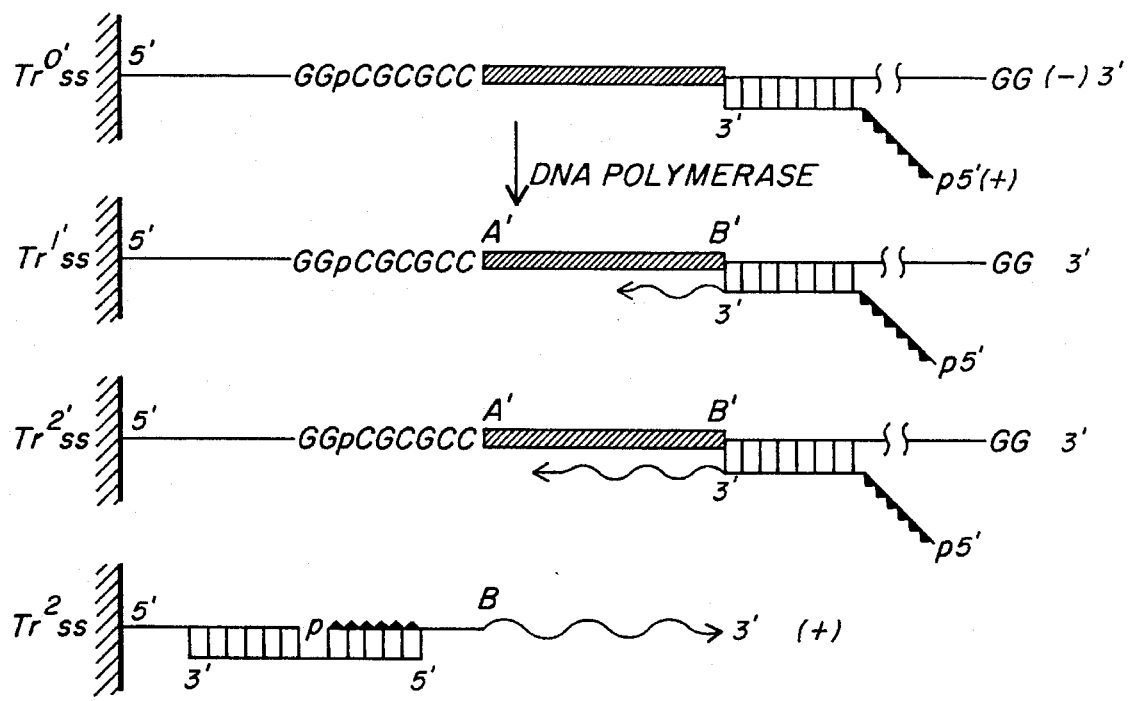

The mass-modification of the immobilized strand starting with the unknown DNA insert in a double-stranded vector (FIG. 4A) can be introduced starting with a situation similar to Tr$^0$ds in FIG. 2. However, a 5' phosphorylated exonuclease III resistant splint oligonucleotide (i.e. 2',3' dideoxy) is ligated to the (−) strand allowing a unilateral digestion of the (+)strand with exonuclease III (FIG. 4A). The mass-modifications are then introduced by a filling-in reaction using template dependent DNA polymerases such as Sequenase, version 2.0 (US Biochemicals), Taq DNA polymerase or AMV reverse transcriptase and appropriate mass-modified dNTPs. In another embodiment one can start with a situation similar to Tr$^0$ss in FIG. 2 and by using a (−) primer designed to bind outside the A boundary at the 3' end of the (+)strand, synthesize a mass-modified (−) strand employing mass-modified dNTPs and a DNA dependent DNA polymerase as described above. In one embodiment, there can be a short stretch of sequence between the Not I and the Asc I site to allow this primer to hybridize effectively. This approach can also be carried out by generating a mass modified (+) strand starting with Tr$^0$ss (FIG. 4B). The newly synthesized (+) strand can be isolated from the (−) strand solid support, such as by denaturation, and immobilized via the 5' sequence information of the primer and a splint oligonucleotide which is in part complementary to this and to an oligonucleotide sequence already attached to another solid support (FIG. 4B). After ligation (i.e. with T4 ligase) the splint oligonucleotide is removed and the immobilized mass-modified single-stranded (+) DNA is transferred to the sequencing reactor (FIG. 9) and contacted with an exonuclease, such as T4 DNA polymerase in solution, for mass spectrometric sequence determination via the released mass-modified nucleotides.

Figure 5:
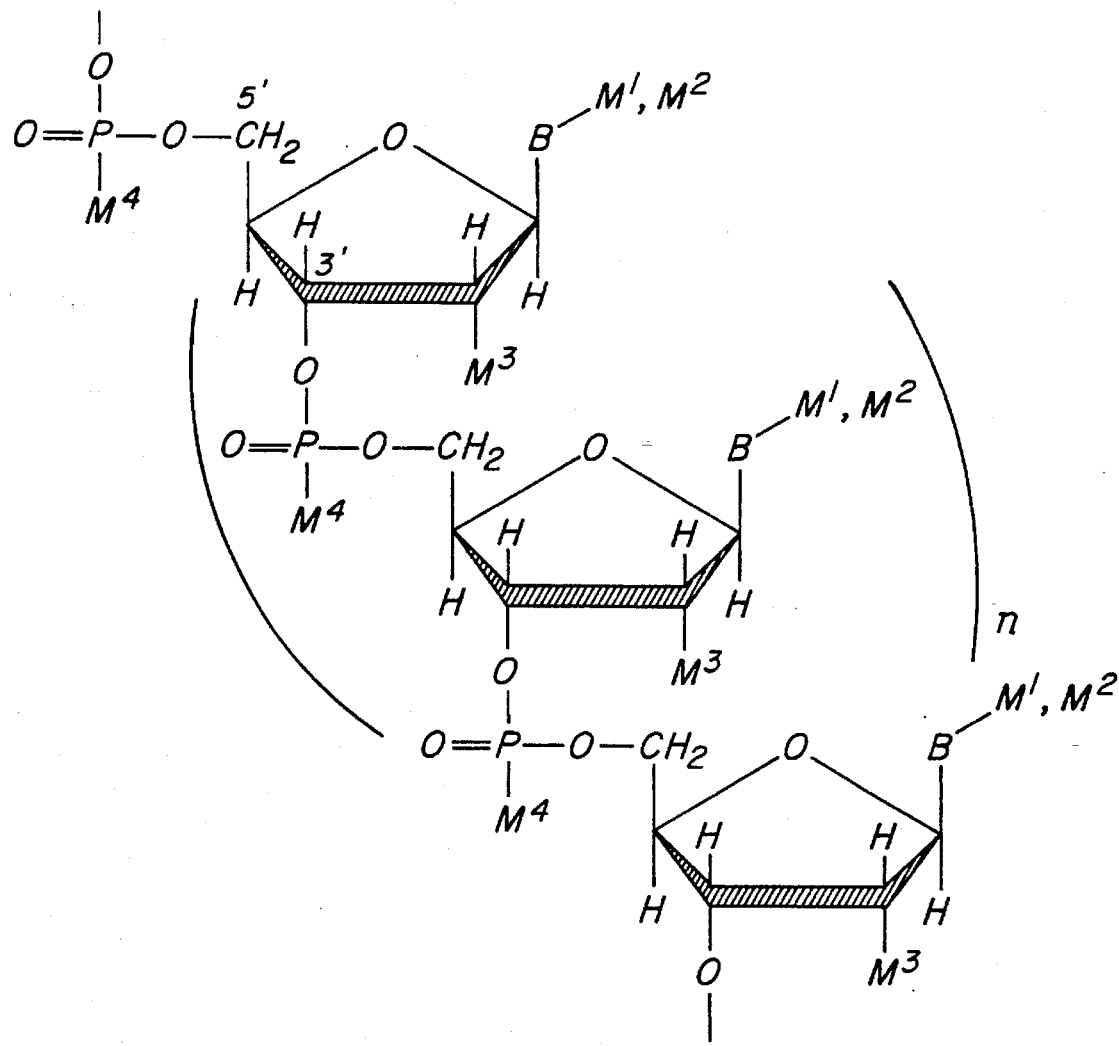
FIG. 5 shows positions within a nucleic acid molecule which can be modified for the introduction of discriminating mass increments or modulation of exonuclease activity.

In accordance with this invention the mass-modifying functionality can be located at different positions within the nucleotide moiety (FIG. 5 and 6). See also H. Köster, U.S. patent application No. 08/001,323, for further examples and synthesis chemistries. For instance, the mass-modifying functionality can be located at the heterocyclic base at position C-8 in purine nucleotides (M1) or C-8 and/or C7 (M2) in c7-deazapurine nucleotides and at C-5 in uracil and cytosine and at the C-5 methyl group at thymine residues (M1). Modifications in these positions do not interfere with Watson-Crick specific base-pairing necessary for the enzymatic incorporation into the mass-modified nucleic acids (DNA/RNA) with high accuracy. Modifications introduced at the phosphodiester bond (M4), such as with alpha-thio nucleoside triphosphates, have the advantage that these modification do not interfere with accurate Watson-Crick base-pairing and additionally allow for the one-step post-synthetic site-specific modification of the complete nucleic acid molecule e.g. via alkylation reactions [K. L. Nakamaye, G. Gish, F. Eckstein and H.-P. Vossberg, *Nucleic Acids Res.*, 16, 9947–59 (1988)]. However, this modification is not applicable where the exonucleolytically released nucleotides are to be treated with immobilized alkaline phosphatase intermediate release and mass spectrometric detection. Mass modification can also occur at the sugar moiety, such as at the position C-2' (M3). Modifications at this position can be introduced with the purpose of modulating the rate of exonuclease activity in order to synchronize the degradation process from time to time. The modification M4 can also serve this purpose. For example, it is known [Burgers and Eckstein, (1979), supra] that a phosphodiester bond carrying a monothio function is approximately 100 time less sensitive towards exonucleolytic degradation by exonuclease III.

Figure 8:
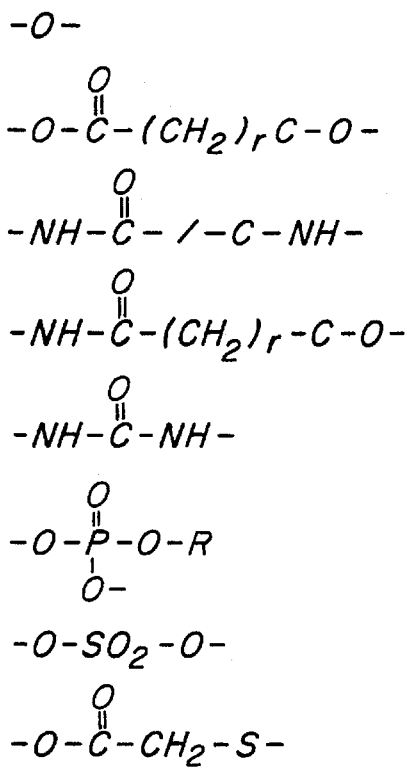
FIG. 8 illustrates some linking groups X for the attachment of the mass modifying functionality R to nucleosides.

The tables in FIGS. 7 and 8 depict some examples of mass-modifying functionalites for nucleotides. This list is, however, not meant to be limiting, since numerous other combinations of mass modifying functions and positions within the nucleotide molecule are possible and are deemed part of the invention. The mass modifying functionality can be, for example, a halogen, an azido, or of the type XR. Wherein X is a linking group and R is a mass modifying functionality. The mass modifying functionality can thus be used to introduce defined mass increments into the nucleotide molecule.

Without limiting the scope of the invention, the mass modification, M, can be introduced for X in XR as well as using oligo-/polyethylene glycol derivatives for R. The mass modifying increment in this case is 44, i.e. five different mass modified species could be generated by just changing m from 0 to 4 thus adding mass units of 45 (m=0), 89 (m=1), 133 (m=2), 177 (m=3) and 221 (m=4). The oligo/polyethylene glycols can also be monoalkylated by a lower alkyl such as methyl, ethyl, propyl, isopropyl, t-butyl and the like. A selection of linking functionalities X are also illustrated in FIG. 8. Other chemistries can be used in the mass modified compounds, as for example, those described recently in Oligonucleotides and Analogues, A Practical Approach, F. Eckstein, editor, IRL Press, Oxford, 1991.

In yet another embodiment, various mass modifying functionalities R, other than oligo/polyethylene glycols, can be selected and attached via appropriate linking chemistries X. A simple mass modification can be achieved by substituting H for halogens like F, Cl, Br and/or I; or pseudohalogens such as SCN, NCS; or by using different alkyl, aryl or aralkyl moieties such as methyl, ethyl, propyl, isopropyl, t-butyl, hexyl, phenyl, substituted phenyl, benzyl; or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another mass modification can be obtained by attaching homo- or heteropeptides through X to the nucleotide. One example useful in generating mass modified species with a mass increment of 57 is the attachment of oligoglycines, e.g. mass modifications of 74 (r=1, m=O), 131 (r=1, m=2), 188 (r=1, m=3), 245 (r=1, m=4) are achieved. Simple oligoamides also could be used, e.g. mass modifications of 74 (r=1, m=0), 88 (r=2, m=0), 102 (r=3, m=0), 116 (r=4, m=0) etc. are obtainable. For those skilled in the art it will be obvious that there are numerous possibilities, for introducing, in a predetermined manner, many different mass modifying functionalities to the nucleotide.

In yet another embodiment of this invention, the mass modifying functionality can be introduced by a two or multiple step process. In this case the nucleotide is, in a first step, modified by a precursor functionality such as azido, $—N_3$, or modified with a functional group in which the R in XR is H thus providing temporary functions e.g. but not limited to —OH, $—NH_2$, —NHR, —SH, —NCS, $—OCO(CH_2)_r COOH$ (r=1–20), $—NHCO(CH_2)_r COOH$ (r=1–20), $—OSO_2OH$, $—OCO(CH_2)_r I$ (r=1–20), $—OP(O-Alkyl)N(Alkyl)_2$. These less bulky functionalities result in better substrate properties for enzymatic DNA or RNA synthesis reactions. The appropriate mass modifying functionality can then be introduced after the generation of the target nucleic acid prior to mass spectrometry and either prior to exonuclease degradation or after release by exonuclease action.

(iii) The exonuclease sequencer:

A schematic outlay of an exonuclease sequencer is shown in FIG. 9. The central part is the reactor S which has a cooling/heating mantle (2) and a frit or semipermeable membrane (4). Several flasks (R1–R5) can be dedicated to supply reagents such as buffer solutions, enzyme, etc. through a cooling/heating coil T. Beneath the reactor S there is a capillary tube E in which either the exonuclease or the nucleic acids can be immobilized. It is within the scope of this invention that there are at least two different modes by which the system can be operated. In one mode, the nucleic acids are immobilized on beads or flat membrane disks placed in the reactor S, or alternatively, immobilized on the inner surface of the walls within the capillary E. Exonuclease is added to the reactor in a controlled manner and the reaction mixture circulated through a loop maintained at a carefully controlled temperature. In a second mode, the exonuclease can be immobilized in e.g. a capillary E beneath the reactor S or could be immobilized on beads or on a membrane or entrapped in a gel or kept in the reactor S by way of a semipermeable membrane. By varying the length and diameter of the capillary and the flow rate through a pumping device P, the contact time of the nucleic acids with the exonuclease can be varied.

In both process modes, aliquots can be fed either continuously or in pulses to the mass spectrometer either directly or through a reactor AP which contains, for instance, immobilized alkaline phosphatase or other mass-modifying reagents. In case the liquid volume which is transferred to the mass spectrometer is too large, only a portion can be supplied while the remainder is separated from the flow stream by using a flow splitting device SP. Unused or excess solutions can be disposed of by the waste container W. In case the reaction mixture of the exonuclease digestion is processed via a moving belt the liquid flow can be directed through this module prior to entering the mass spectrometer.

(iv) The exonuclease sequencing process:

Various exonucleases can be used, such as snake venom phosphodiesterase, Bal-31 nuclease, *E. coli* exonuclease VII, Mung Bean Nuclease, S1 Nuclease, exonuclease and exonuclease III as well as the exonuclease activity of some DNA polymerases such as *E. coli* DNA polymerase I, the Klenow fragment of DNA polymerase I, T4 or T7 DNA polymerases, Taq DNA polymerase, Deep Vent DNA polymerase, and Vent$_r$ DNA polymerase. The activity of these exonucleases can be modulated, for instance, by shifting off the optimal pH and/or temperature range or by adding poisoning agents to the reaction mixture. The exonuclease activity can also be modulated by way of functional groups, such as at the C-2' position of the sugar moiety of the nucleotide building block or at the phosphodiester bond (i.e. M3/M4 in FIG. 5 and 6).

Figure 10:
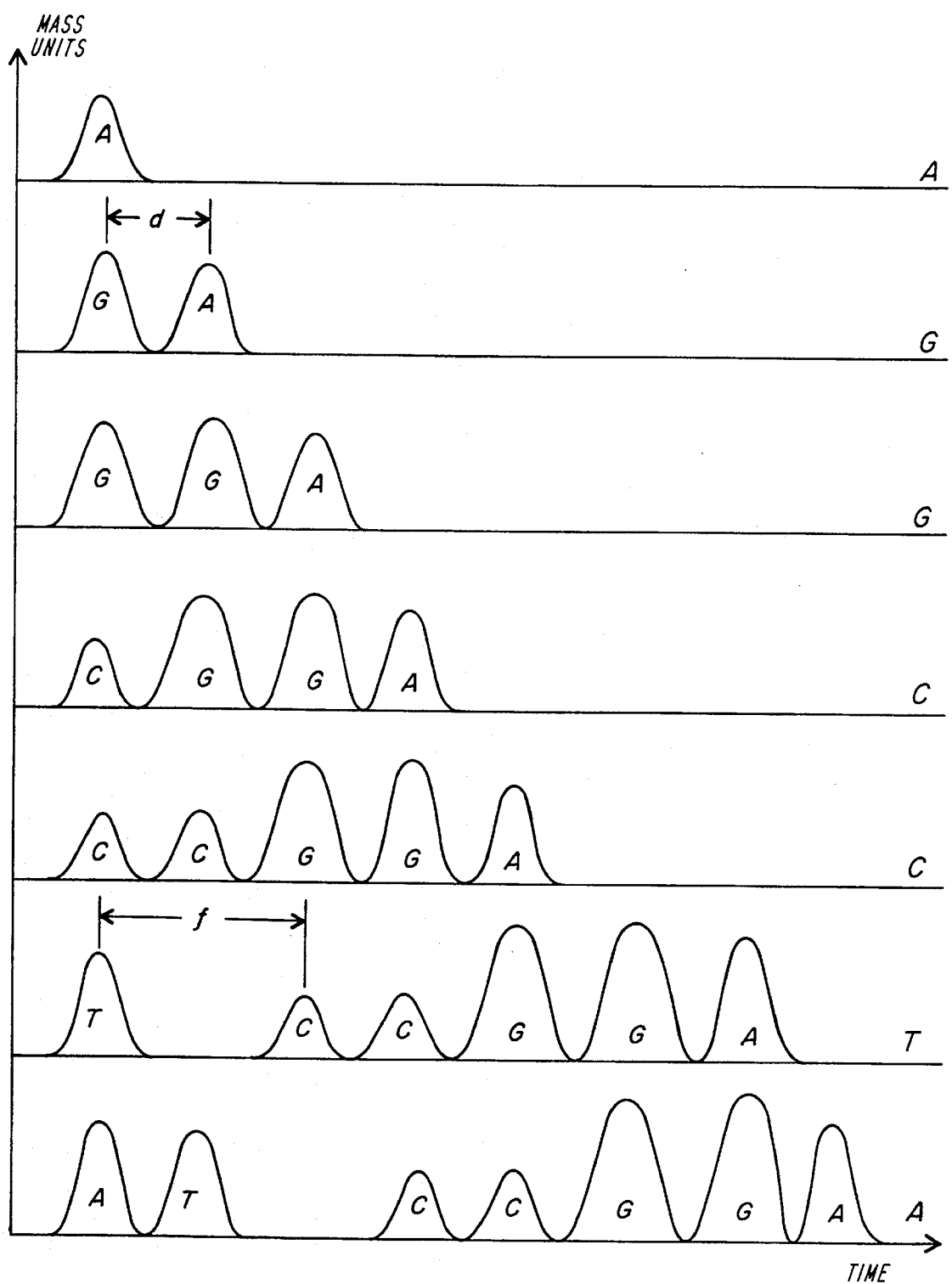
FIG. 10 is a graphical representation of idealized output signals following the time-course of the stepwise mass spectrometric detection of the exonucleolytically released nucleotides.

In the instance that unmodified nucleotides are detected, the masses for the phosphate dianion are 329.209 for pdG, 313.210 for pdA, 304.196 for pdT and 289.185 for pdC. In an idealized system the enzymatic digestion would be initiated at all nucleic acid chains at the same time, and the nucleotides would be released in identical time intervals d and detected by their individual molecular weights one after the other by the mass spectrometer. FIG. 10 illustrates the signals versus time for the sequence 5'. . . A-T*-Co C-G-G-A 3'.

The influence of an activity modulating functionality M3/M4 on appropriately modified thymidine, T*, is also depicted. Due to the drastically reduced cleavage rate of the phosphodiester bond between dC and dT* the molecular mass representing the T* signal appears after a longer time interval fi The significant retardation of the cleavage rate of one type of nucleotide results in better overall synchronization of the enzymatic process. This retardative effect can be varied to a large extent by the bulkiness of the modifying functional group as well as by a possible interaction with the active site of the exonuclease. Additionally, partial overlap of signals can be resolved by computational methods.

Figure 11:
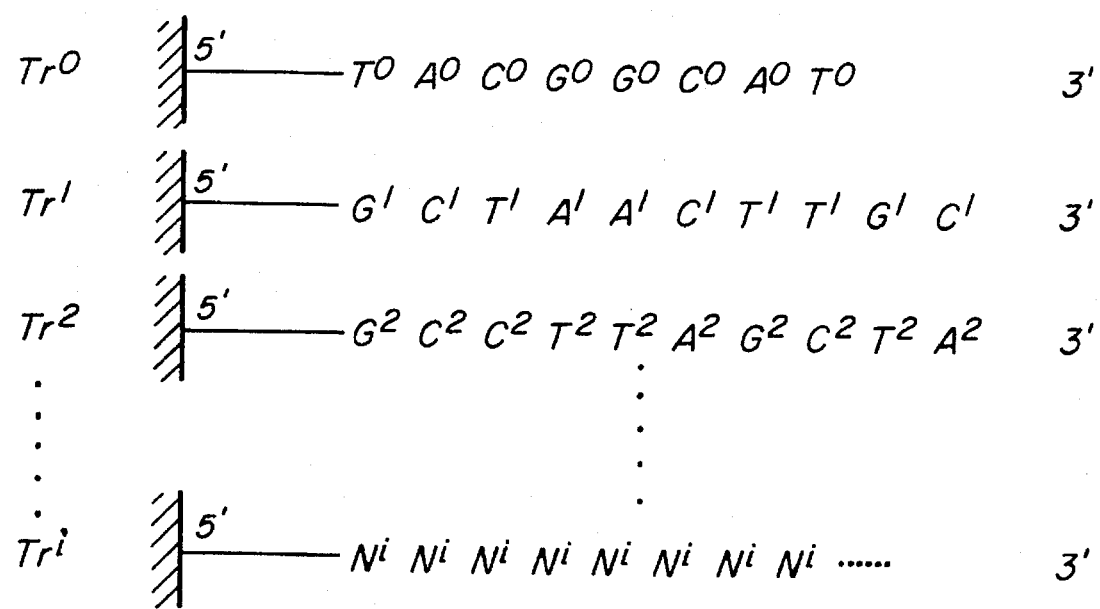
FIG. 11 illustrates specific labels introduced by mass modification to facilitate multiplex exonuclease mass spectrometric sequencing.

(v) Multiplex exonuclease sequencing:

A significant increase in throughput can be further obtained by employing the principle of multiplex exonuclease sequencing. The principle of this concept is illustrated in FIG. 11. For multiplex mass spectrometric exonuclease DNA sequencing, the DNA fragments to be processed in parallel can be identified by fragment specific labels introduced by the mass modifying functionality M. The target nucleic acid sequences can be mass-modified by using, for example, unmodified $dNTP^0$s or $NTP^0$s (Tr0), nucleoside triphosphates mass-modified with the same functional group, such as an additional methyl group at the heterocyclic base, using either $dNTP^1$ or $NTP^1$ (Tr0), mass difference large enough to be discriminated from the nucleotides of Tr0 or Tr1, such as e.g. an ethyl group at the heterocyclic base, by employing either $dNTP^2$ or $NTP^2$ etc. Thus i modified DNA fragments can be simultaneously exonuclease sequenced. For example, the i different DNA fragments can be immobilized on different membranes and a stack of such membranes placed into the reactor S (FIG. 9) for simultaneous exonuclease mass spectrometric sequencing. Since the individual molecular weights of the various mass-modified four nucleotides are known in advance, the mass spectrometrically detected nucleotide masses can be easily assigned to the parent nucleic acid fragments and thus several sequences can be detected simultaneously by the mass spectrometer. Even in the worst case when the same nucleotide, e.g. dT is at the same position in all sequences, processed in parallel the signal can be decoded due to the difference in mass between $dT^0$, $dT^1$, $dT^2$, $dT^3$, . . . , $dT^i$ The synchronization of exonuclease action can be improved by incorporating modified nucleotides (modified at C-2' or at the phosphodiester bond) into the otherwise unmodified or mass-modified nucleic acid fragments as set out above. In particular such a mass-modified nucleotide can also be introduced at the 3' end of the single stranded nucleic acid fragment (i.e. C-2' or phosphodiester bond modifications) to achieve a more uniform initiation of the exonuclease reaction.

Figure 12:
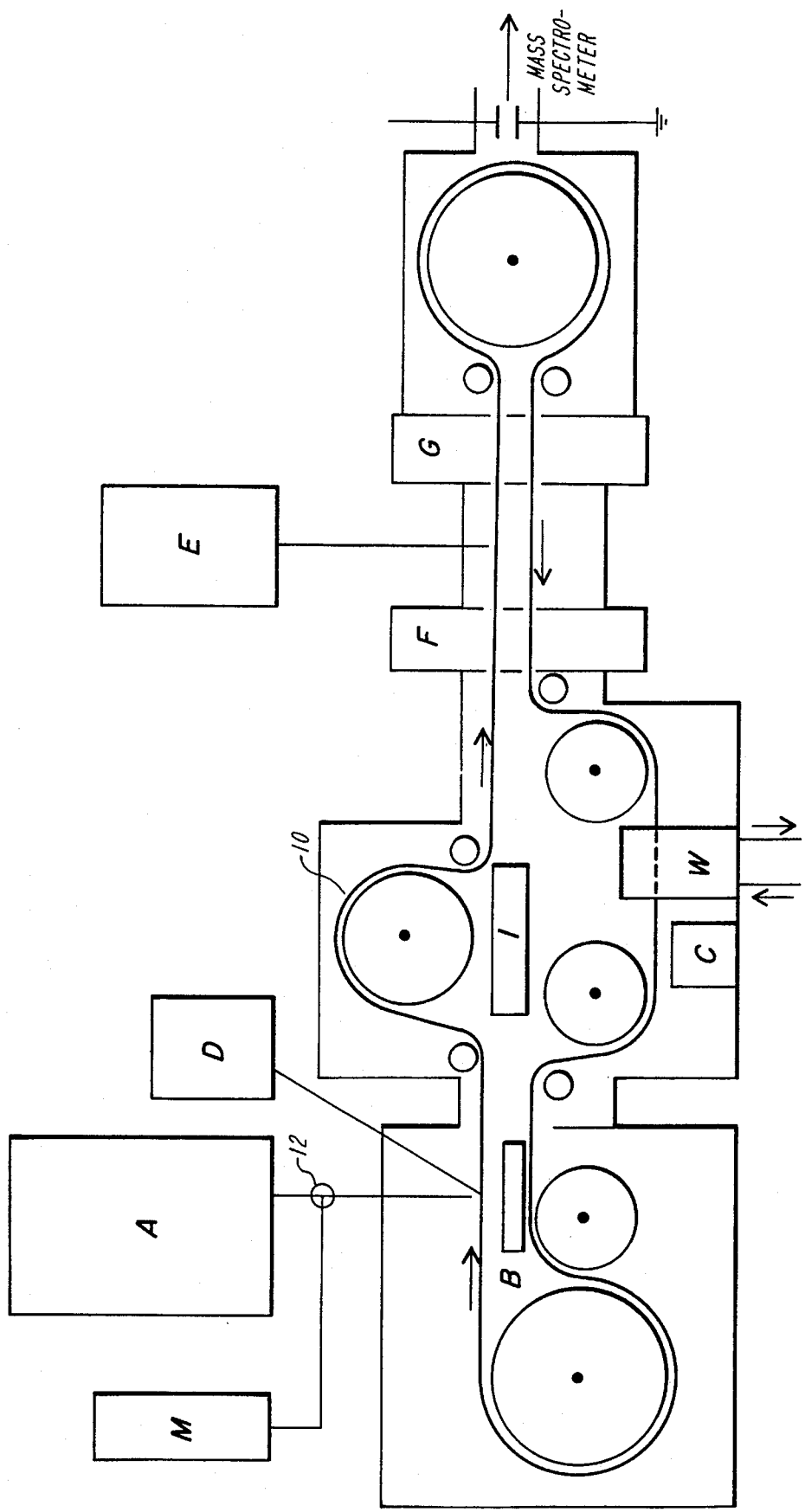
FIG. 12 is a schematic drawing of a moving belt apparatus for delivering single or multiple tracks of exonuclease samples for laser induced mass spectrometric sequence determination in conjunction with the sequencing reactor of FIG. 9.
Figure 13:
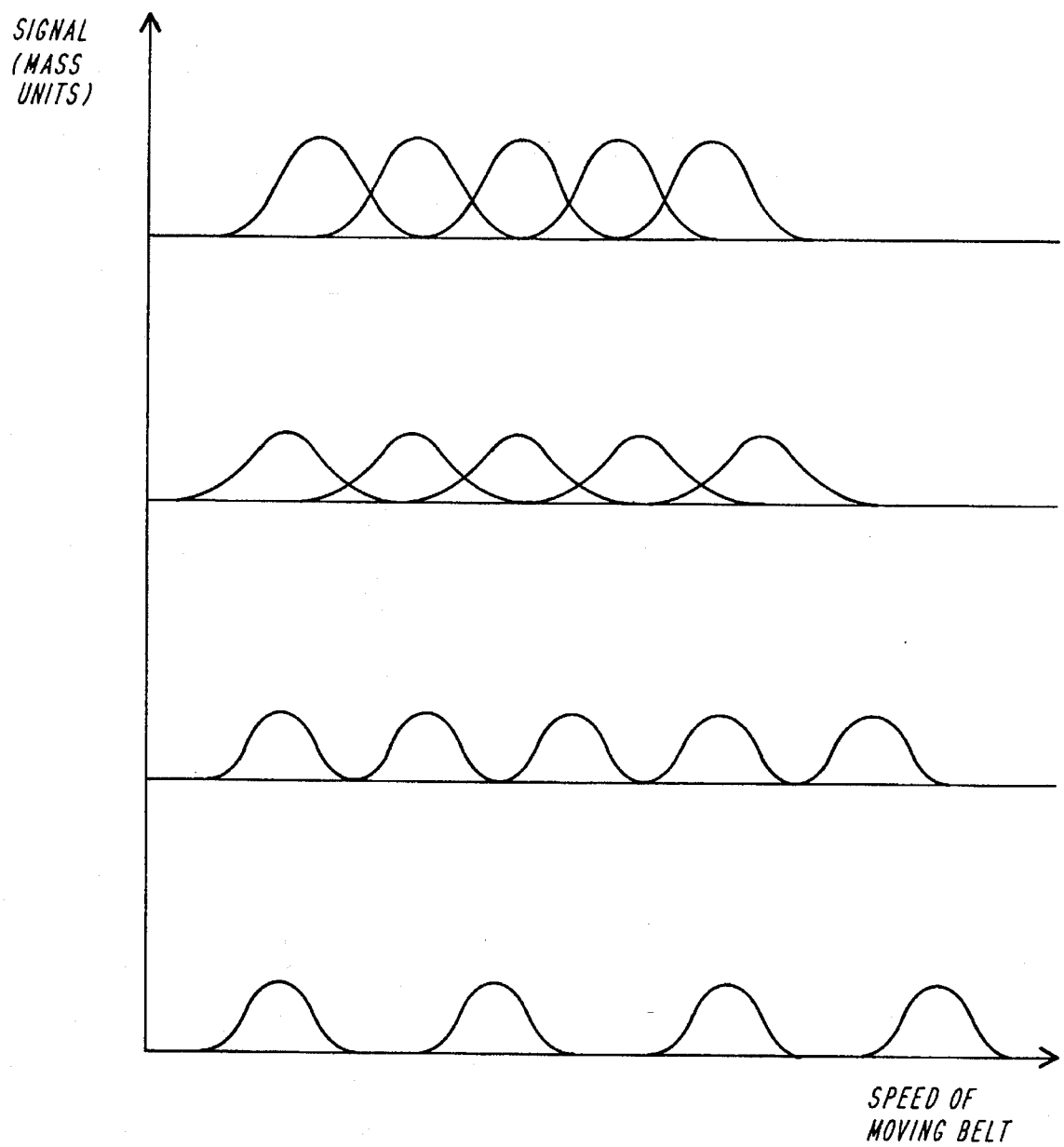
FIG. 13 is a schematic representation of individually labeled signal tracks employed in multiplex exonuclease mediated mass spectrometric sequencing.

In yet another embodiment of this invention, a reduction of overlap of neighboring signals can be achieved by using a moving belt device as schematically shown in FIG. 12. In a recent publication a moving belt has been described although in a completely unrelated application [M. Moini and F. P. Abramson, *Biological Mass Spectrometry*, 20, 308–12 (1991)]. The effect of the moving belt can be to help spread the appearance of sequentially released nucleotide/nucleoside signals as illustrated in FIG. 13. The width between consecutive, i.e. neighboring, signals can be increased with the speed of the moving belt.

Without limiting the scope of the invention FIG. 12 illustrates a possible configuration of the moving belt module for exonuclease mediated mass spectrometric sequencing. An endless metal ribbon (10) is driven with variable speed using a controllable stepping motor and appropriately positioned pulleys. Spring-loaded pulleys can be used to maintain a sufficiently high tension on the moving belt. The sample is applied to the belt from the reactor module A (FIG. 9) at a position which is in direct contact with a cooling/heating plate B. In case matrix-assisted laser desorption/ionization mass spectrometry is employed the sample can be mixed with a matrix solution M prior to loading onto the belt. Crystal formation can be observed with a viewing device D (CCD camera and optics). Alternatively the container M can be used to mix the sample with a diluent or other reagent, enzyme, internal standard etc. at a mixing valve or vortex (12). In the instance of relatively small molecules such as the released nucleotides, matrix is not essential for the laser desorption/ionization process to take place. The belt 10 moves the sample under a laser source E (with appropriate optics) for desorption and ionization.

A heating element C, such as a microwave source, can be placed near the surface of the returning belt, separated from the forward moving belt by an insulating shield I, to clean the surface of the metal ribbon belt 10 of any organic material prior to loading a new sample. Alternatively, a washing station W can be integrated before the heating element C; in this case the function of the heating element C can be completely dry the metal ribbon prior to reloading of sample. Before and after the laser targets the sample, two differential vacuum pumping stages F and G are positioned. An electric field is applied after the second vacuum stage to accelerate the ions into the mass spectrometer. As mass analyzer, a quadrupole can be used, though other mass analyzing configurations are known in the art and are within the scope of the invention. The design of the vacuum interface of the moving belt between the sample application compartment which is at atmospheric pressure, and the mass spectrometer can be important. In one approach, this vacuum seal can be provided by the use of tunnel seals in a two-stage vacuum lock as previously described [Moini et al, (1991), supra].

As described above, an increase of throughput can be obtained by multiplexing. In yet another embodiment of the invention the moving belt device can be used for a second dimension in multiplexing by applying s samples from s sequencing reactors A (FIG. 9) simultaneously in different locations onto the moving belt. Desorption and ionization of these multiple samples is achieved by moving the laser beam with adjustable speed and frequency back and forth perpendicular to the direction of the moving belt. Identification and assignment of the nucleotides/nucleosides detected to the various nucleic acid fragments can be achieved by second dimension multiplexing, i.e. by mass-labeling the nucleic acid fragments with for example $—CH_2—$, $—CH_2CH_2—$, $—CH_2CH_2CH_2—$ and $—CH_2(CH_2)_rCH_2—$, and labeling the different reactors, for example, by individual halogen atoms, i.e. F for reactor 1 (thus having the different DNA fragments labeled with $—CH_2F$, $—CH_2CH_2F$, $—CH_2CH_2CH_2F$, $—CH_2(CH_2)_rCH_2F$), Cl for reactor 2 (thus having the different DNA fragments labeled with $—CH_2Cl$, $—CH_2CH_2Cl$, $—CH_2CH_2CH_2Cl$, $—CH_2(CH_2)_rCH_2Cl$), Br for reactor 3 etc. This can increase the throughput dramatically. Two-dimensional multiplexing can be applied in different ways. For example, it can be used to simultaneously sequence the fragments forming one set of overlapping deletions of the same long DNA insert. In another embodiment, several subsets of ordered deletions of different DNA inserts can be analyzed in parallel.

The enormous advantage of exonuclease mediated mass spectrometric DNA sequencing is that small molecules are analyzed and identified by mass spectrometry. In this mass range, the accuracy of mass spectrometers is routinely very high, i.e. 0.1 mass units are easily detected. This increases the potential for multiplexing as small differences in mass can be detected and resolved. An additional advantage of mass spectrometric sequencing is that the identified masses can be registered automatically by a computer and by adding the time coordinate automatically aligned to sequences. Since the sequences so determined are memorized (i.e. saved to disk or resident in the computer memory) appropriate existing computer programs operating in a multitasking environment can be searching in the "background" (i.e. during continuous generation of new sequence data by the exonuclease mass spectrometric sequencer) for overlaps and generate contiguous sequence information which, via a link to a sequence data bank, can be used in homology searches, etc.

Another aspect of this invention concerns kits for sequencing nucleic acids by exonuclease mass spectrometry, which include combinations of the above described sequencing reactants. For instance, in one embodiment, the kit comprises reagents for multiplex mass spectrometric sequencing of several different species of nucleic acid. The kit can include an exonuclease for cleaving the nucleic acids unilaterally from a first end to sequentially release individual nucleotides, a set of nucleotides for synthesizing the different species of nucleic acids, at least a portion of the nucleotides being mass-modified such that sequentially released nucleotides of each of the different species of nucleic acids are distinguishable, a polymerase for synthesizing the nucleic acids from complementary templates and the set of nucleotides, and a solid support for immobilizing one of the nucleic acids or the exonuclease. The kit can also include appropriate buffers, as well as instructions for performing multiplex mass spectrometry to concurrently sequence multiple species of nucleic acids. In another embodiment, the sequencing kit can include an exonuclease for cleaving a target nucleic acid unilaterally from a first end to sequentially release individual nucleotides, a set of nucleotides for synthesizing the different species of nucleic acids, at least a portion of the nucleotides being mass-modified to modulate the exonuclease activity, a polymerase for synthesizing the nucleic acid from a complementary template and the set of nucleotides, and a solid support for immobilizing one of the nucleic acids or the exonuclease.

Another aspect of this invention concerns a "reverse-Sanger" type sequencing method using exonuclease digestion of nucleic acids to produce a ladder of nested digestion fragments detectable by mass spectrometry. For instance, as above, the target nucleic acid can be immobilized to a solid support to provide unilateral degradation of the chain by exonuclease action. Incorporating into the target nucleic acid a limited number of mass-modified nucleotides which inhibit the exonuclease activity (i.e. protect an individual nucleic acid chain from further degradation) can result in a ladder of nested exonuclease fragments. See Labeit et al. (1986) *DNA* 5: 173; Eckstein et al. (1988) *Nucleic Acid Res.* 16: 9947; and PCT Application No. GB86/00349. The nested exonuclease fragments can then be released from the solid support (i.e. via a cleavable linkage) and the molecular weight values for each species of the nested fragments determined by mass spectrometry, as described in U.S. patent application No. 08/001,323. From the molecular weight values determined, the sequence of the nucleic acid can be generated. It is clear that many variations of this reaction are possible and that it is amenable to multiplexing. For example, the target nucleic acid need not be bound to a solid support, rather any protecting group can be used to ensure unilateral exonuclease degradation. Where mass-modified nucleotides are used which have large enough molecular weight differences to be differentiated between by mass spectrometry (i.e. the termination of a chain with a particular mass-modified nucleotide is discernable from all other terminations), the exonuclease sequencing can be carried out to create only one set of nested fragments. Alternatively, individual types of exonuclease-inhibiting nucleotides can be incorporated in separate reactions to create sets of nested fragments. For instance, four sets of nested fragments can be separately generated wherein one set terminates with mass-modified A's, one set terminates in mass-modified G's, etc. and the total sequence is determined by aligning the collection of nested exonuclease fragments.

EXAMPLE 1

Immobilization of nucleic acids to solid supports via disulfide bonds.

As a solid support, SEQUELON™ membranes (Millipore Corp., Bedford, Mass.) with phenyl isothiocyanate groups is used as a starting material. The membrane disks, with a diameter of 8 mm, are wetted with a solution of N-methyl-morpholine/water/2-propanol (NMM solution) (2/49/49;v/v/v), the excess liquid removed with filterpaper and placed on a piece of plastic film or aluminium foil located on a heating block set to 55° C. A solution of 1 mM 2-mercaptoethylamine (cysteamine) or 2,2'-dithio-bis(ethylamine) (cystamine) or S-(2-thiopyridyl)-2-thio-ethylamine (10 ul, 10 nmol) in NMM is added per disk and heated at 55° C. After 15 min 10 ul of NMM solution are added per disk and heated for another 5 min. Excess of isothiocyanate groups may be removed by treatment with 10 ul of a 10 mM solution of glycine in NMM solution. In case of cystamine the disks are treated with 10 ul of a solution of 1M aqueous dithiothreitol (DTT)/2-propanol (1:1, v/v) for 15 min at room temperature. Then the disks are thoroughly washed in a filtration manifold with 5 aliquots of 1 ml each of the NMM solution, then with 5 aliquots of 1 ml acetonitrile/water (1/1; v/v) and subsequently dried. If not used immediately the disks are stored with free thiol groups in a solution of 1M aqueous dithiothreitol/2-propanol (1:1; v/v) and, before use, DTT is removed by three washings with 1 ml each of the NMM solution. Single-stranded nucleic acid fragments with 5'-SH functionality can be prepared by various methods [e.g. B.C.F Chu et al., Nucl eic Acids Res., 14, 5591–5603 (1986), Sproat et al., Nucleic Acids Res., 15, 4837–48 (1987) and Oligonucleotides and Analogues. A Practical Approach (F. Eckstein editor), IRL Press Oxford, 1991]. The single-stranded nucleic acid fragments with free 5'-thiol group are now coupled to the thiolated membrane supports under mild oxidizing conditions. In general it is sufficient to add the 5'-thiolated nucleic acid fragments dissolved in 10 ul 10 mM de-aerated triethylammonium acetate buffer (TEAA) pH 7.2 to the thiolated membrane supports; coupling is achieved by drying the samples onto the membrane disks with a cold fan. This process can be repeated by wetting the membrane with 10 ul of 10 mM TEAA buffer pH 7.2 and drying as before. When using the 2-thiopyridyl derivatized compounds anchoring can be monitored by the release of pyridine-2-thione spectrophotometrically at 343 nm.

In another variation of this approach the single-stranded nucleic acid is functionalized with an amino group at the 5'-end by standard procedures. The primary amino group is reacted with 3-(2-pyridyldithio)propionic acid N-hydroxysuccinimide ester (SPDP) and subsequently coupled to the thiolated supports and monitored by the release of pyridyl-2-thione as described above. After denaturation of any remaining protein and ethanol precipitation of the functionalized nucleic acid, the pellet is dissolved in 10 ul 10 mM TEAA buffer pH 7.2 and 10 ul of a 2 mM solution of SPDP in 10 mM TEAA are added. The reaction mixture is vortexed and incubated for 30 min at 25° C.; excess SPDP is then removed by three extractions (vortexing, centrifugation) with 50 ul each of ethanol and the resulting pellets dissolved in 10 ul 10 mM TEAA buffer pH 7.2 and coupled to the thiolated supports (see above).

The imobilized nucleic acids can be released by three successive treatments with 10 ul each of 10 mM 2-mercaptoethanol in 10 mM TEAA buffer pH 7.2.

EXAMPLE 2

Immobilization of nucleic acids on solid support via a levulinyl group

5-Aminolevulinic acid is protected at the primary amino group with the Fmoc group using 9-fluorenylmethyl N-succinimidyl carbonate and then transformed into the N-hydroxysuccinimide ester (NHS ester) using N-hydroxysuccinimide and dicyclohexyl carbodiimide under standard conditions. Nucleic acids which are functionalized with primary amino acid at the 5' end are EtOH precipitated and resuspended in 10 ul of 10 mM TEAA buffer pH 7.2. 10 ul of a 2 mM solution of the Fmoc-5-aminolevulinyl-NHS ester in 10 mM TEAA buffer is added, vortexed and incubated at 25° C. for 30 min. The excess of reagents can be removed by ethanol precipitation and centrifugation. The Fmoc group is cleaved off by resuspending the pellets in 10 ul of a solution of 20% piperidine in N,N-dimethylformamide/water (1:1, v/v). After 15 min at 25° C. piperidine is thoroughly removed by three precipitations/centrifugations with 100 ul each of ethanol, the pellets resuspended in 10 ul of a solution of N-methylmorpholine, propanol-2 and water (2/10/88; v/v/v) and coupled to the solid support carrying an isothiocyanate group. In case of the DITC-Sequelon membrane (Millipore Corp., Bedford, Mass.) the membranes are prepared as described in EXAMPLE 1 and coupling is achieved on a heating block at 55° C. as described above. The procedure can be applied to other solid supports with isothiocyanate groups in a similar manner.

The immobilized nucleic acids can be released from the solid support by three successive treatments with 10 ul of 100 mM hydrazinium acetate buffer pH 6.5.

EXAMPLE 3

Immobilization of nucleic acids on solid supports via a trypsin sensitive linkage.

Sequelon DITC membrane disks of 8 mm diameter (Millipore Corp. Bedford, Mass.) are wetted with 10 ul of NMM solution (N-methylmorpholine/propanaol-2/water; 2/49/49;v/v/v) and a linker arm introduced by reaction with 10 ul of a 10 mM solution of 1,6-diaminohexane in NMM. The excess of the diamine is removed by three washing steps with 100 ul of NMM solution. Using standard peptide synthesis protocols two L-lysine residues are attached by two successive condensations with N-Fmoc-N-tBoc-L-lysine pentafluorophenylester, the terminal Fmoc group is removed with piperidine in NMM and the free ε-amino group coupled to 1,4-phenylene diisothiocyanate (DITC). Excess DITC is removed by three washing steps with 100 ul propanol-2 each and the N -tBoc groups removed with trifluoroacetic acid according to standard peptide synthesis procedures. The nucleic acids are prepared from as above from a primary amino group at the 5'-terminus. The ethanol precipitated pellets are resuspended in 10 ul of a solution of N-methylmorpholine, propanol-2 and water (2/10/88; v/v/v) and transferred to the Lys-Lys-DITC membrane disks and coupled on a heating block set at 55° C. After drying 10 ul of NMM solution is added and the drying process repeated.

The immobilized nucleic acids can be cleaved from the solid support by treatment with trypsin.

EXAMPLE 4

Immobilization of nucleic acids on solid supports via pyrophosphate linkage.

The DITC Sequelon membrane (disks of 8 mm diameter) are prepared as described in EXAMPLE 3 and 10 ul of a 10 mM solution of 3-aminopyridine adenine dinucleotide (APAD) (Sigma) in NMM solution added. The excess of APAD is removed by a 10 ul wash of NMM solution and the disks are treated with 10 ul of 10 mM sodium periodate in NMM solution (15 min, 25° C.). Excess of periodate is removed and the having a primary amino group at the 5'-end are dissolved in 10 ul of a solution of N-methylmorpholine/propanol-2/water (2/10/88; v/v/v) and coupled to the 2',3'-dialdehydo functions of the immobilized NAD analog.

The ommobilized nucleic acids can be released from the solid support by treatment with either NADase or pyrophosphatase in 10 mM TEAA buffer at pH 7.2 at 37° C. for 15 min.

EXAMPLE 5

Synthesis of pyrimidine nucleotides mass modified at C-5 of the heterocyclic base with glycine residues.

Starting material is 5-(3-aminopropynyl-1)-3',5'-di-p-tolyldeoxyuridine prepared and 3',5'-de-O-acylated according to literature procedures [Haralambidis et al., Nucleic Acids Res., 15, 4857–76 (1987)]. 0.281 g (1.0 mmole) 5-(3-aminopropynyl-1)-2'-deoxyuridine are reacted with 0.927 g (2.0 mmole) N-Fmoc-glycine pentafluorophenylester in 5 ml absolute N,N-dimethylformamide in the presence of 0.129 g (1 mmole; 174 ul) N,N-diisopropylethylamine for 60 min at room temperature. Solvents are removed by rotary evaporation and the product purified by silica gel chromatography (Kieselgel 60, Merck; column: 2.5×50 cm, elution with chloroform/methanol mixtures). Yield 0.44 g (0.78 mmole, 78%). In order to add another glycine residue the Fmoc group is removed with a 20 min treatment with 20% solution of piperidine in DMF, evaporated in vacuo and the remaining solid material extracted three times with 20 ml ethylacetate; after having removed the remaining ethylacetate N-Fmoc-glycine pentafluorophenylester is being coupled as described above. This glycine modified thymidine analogue building block for chemical DNA synthesis can be used to substitute for thymidine or uridine nucleotides in the target nucleic acid.

EXAMPLE 6

Synthesis of pyrimidine nucleotides mass modified at C-5 of the heterocyclic base with β-alanine residues.

Starting material is the same as in EXAMPLE 5. 0.281 g (1.0 mmole) 5-(3-Aminopropynyl-1)-2'-deoxyuridine is reacted with N-Fmoc-β-alanine pentafluorophenylester (0.955 g, 2.0 mmole) in 5 ml N,N-dimethylformamide (DMF) in the presence of 0.129 g (174 ul; 1.0 mmole)

N,N-diisopropylethylamine for 60 min at room temperature. Solvents are removed and the product purified by silica gel chromatography as described in EXAMPLE 6. Yield: 0.425 g (0.74 mmole, 74%). Another β-alanine moiety could be added in exactly the same way after removal of the Fmoc group. This building block can be substitute for any of the thymidine or uridine residues in the target nucleic acid.

EXAMPLE 7

Synthesis of a pyrimidine nucleotide mass modified at C-5 of the heterocyclic base with ethylene glycol monomethyl ether.

As nucleosidic component 5-(3-aminopropynyl-1)-2'-deoxyuridine is used in this example (see EXAMPLE 5 and 6). The mass-modifying functionality is obtained as follows: 7.61 g (100.0 mmole) freshly distilled ethylene glycol monomethyl ether dissolved in 50 ml absolute pyridine is reacted with 10.01 g (100.0 mmole) recrystallized succinic anhydride in the presence of 1.22 g (10.0 mmole) 4-N,N-dimethylaminopyridine overnight at room temperature. The reaction is terminated by the addition of water (5.0 ml), the reaction mixture evaporated in vacuo, co-evaporated twice with dry toluene (20 ml each) and the residue redissolved in 100 ml dichloromethane. The solution is extracted successively, twice with 10% aqueous citric acid (2×20 ml) and once with water (20 ml) and the organic phase dried over anhydrous sodium sulfate. The organic phase is evaporated in vacuo, the residue redissolved in 50 ml dichloromethane and precipitated into 500 ml pentane and the precipitate dried in vacuo. Yield: 13.12 g (74.0 mmole; 74%). 8.86 g (50.0 mmole) of succinylated ethylene glycol monomethyl ether is dissolved in 100 ml dioxane containing 5% dry pyridine (5 ml) and 6.96 g (50.0 mmole) 4-nitrophenol and 10.32 g (50.0 mmole) dicyclohexylcarbodiimide is added and the reaction run at room temperature for 4 hours. Dicyclohexylurea is removed by filtration, the filtrate evaporated in vacuo and the residue redissolved in 50 ml anhydrous DMF. 12.5 ml (about 12.5 mmole 4-nitrophenylester) of this solution is used to dissolve 2.81 g (10.0 mmole) 5-(3-aminopropynyl-1)-2'-deoxyuridine. The reaction is performed in the presence of 1.01 g (10.0 mmole; 1.4 ml) triethylamine at room temperature overnight. The reaction mixture is evaporated in vacuo, co-evaporated with toluene, redissolved in dichloromethane and chromatographed on silicagel (Si60, Merck; column 4×50 cm) with dichloromethane/methanol mixtures. The fractions containing the desired compound are collected, evaporated, redissolved in 25 ml dichloromethane and precipitated into 250 ml pentane.

EXAMPLE 8

Synthesis of pyrimidine nucleotides mass-modified at C-5 of the heterocyclic base with diethylene glycol monomethyl ether.

Nucleosidic starting material is as in previous examples, 5-(3-aminopropynyl-1)-2'-deoxyuridine. The mass-modifying functionality is obtained similar to EXAMPLE 7. 12.02 g (100.0 mmole) freshly distilled diethylene glycol monomethyl ether dissolved in 50 ml absolute pyridine is reacted with 10.01 g (100.0 mmole) recrystallized succinic anhydride in the presence of 1.22 g (10.0 mmole) 4-N,N-dimethylaminopyridine (DMAP) overnight at room temperature. The work-up is as described in EXAMPLE 7. Yield: 18.35 g (82.3 mmole, 82.3%). 11.06 g (50.0 mmole) of succinylated diethylene glycol monomethyl ether is transformed into the 4-nitrophenylester and subsequently 12.5 mmole reacted with 2.81 g (10.0 mmole) of 5-(3-aminopropynyl-1)-2'-deoxyuridine as described in EXAMPLE 7. Yield after silica gel column chromatography and precipitation into pentane: 3.34 g (6.9 mmole, 69%).

EXAMPLE 9

Synthesis of deoxyadenosine mass-modified at C-8 of the heterocyclic base with glycine.

Starting material is N6-benzoyl-8-bromo-5'-O-(4,4'-dimethoxytrityl)-2'-deoxyadenosine prepared according to literature [Singh et al., Nucleic Acids Res. 18, 3339–45 (1990)]. 632.5 mg (1.0 mmole) of this 8-bromodeoxyadenosine derivative is suspended in 5 ml absolute ethanol and reacted with 251.2 mg (2.0 mmole) glycine methyl ester (hydrochloride) in the presence of 241.4 mg (2.1 mmole; 366 ul) N,N-diisopropylethylamine and refluxed until the starting nucleosidic material has disappeared (4–6 hours) as checked by thin layer chromatography (TLC). The solvent is evaporated and the residue purified by silica gel chromatography (column 2.5×50 cm) using solvent mixtures of chloroform/methanol containing 0.1% pyridine. The product fractions are combined, the solvent evaporated, dissolved in 5 ml dichloromethane and precipitated into 100 ml pentane. Yield: 487 mg (0.76 mmole, 76%).

EXAMPLE 10

Synthesis of deoxyadenosine mass-modified at C-8 of the heterocyclic base with glycylglycine.

This derivative is prepared in analogy to the glycine derivative of EXAMPLE 9. 632.5 mg (1.0 mmole) N6-Benzoyl-8-bromo-5'-O-(4,4'-dimethoxytrityl)-2'-deoxy adenosine is suspended in 5 ml absolute ethanol and reacted with 324.3 mg (2.0 mmole) glycyl-glycine methyl ester in the presence of 241.4 mg (2.1 mmole, 366 ul) N,N-diisopropylethylamine. The mixture is refluxed and completeness of the reaction checked by TLC. Work-up and purification is similar as described in EXAMPLE 9. Yield after silica gel column chromatography and precipitation into pentane: 464 mg (0.65 mmole, 65%).

EXAMPLE 11

Synthesis of deoxythymidine mass-modified at the C-2' of the sugar moiety with ethylene glycol monomethyl ether residues.

Starting material is 5'-O-(4,4-dimethoxytrityl)-2'-amino-2'-deoxythymidine synthesized according to published procedures [e.g. Verheyden et al., J. Org. Chem., 36, 250–254 (1971); Sasaki et al., J. Org. Chem., 41, 3138–3143 (1976); Imazawa et al., J. Org. Chem., 44, 2039–2041 (1979); Hobbs et al., J. Org. Chem., 42, 714–719 (1976); Ikehara et al., Chem. Pharm. Bull. Japan, 26, 240–244 (1978); see also PCT Application WO 88/00201]. 5'-O-(4,4-Dimethoxytrityl)-2'-amino-2'-deoxythymidine (559.62 mg; 1.0 mmole) is reacted with 2.0 mmole of the 4-nitrophenyl ester of succinylated ethylene glycol monomethyl ether (see EXAMPLE 7) in 10 ml dry DMF in the presence of 1.0 mmole (140 ul) triethylamine for 18 hours at room temperature. The reaction mixture is evaporated in vacuo, co-evaporated with toluene, redissolved in dichloromethane and purified by silica gel chromatography (Si60, Merck, column: 2.5×50 cm; eluent: chloroform/methanol mixtures containing 0.1% triethylamine). The product containing fractions are combined, evaporated and precipitated into pentane. Yield: 524 mg (0.73 mmol; 73%).

In an analogous way, employing the 4-nitrophenyl ester of succinylated diethylene glycol monomethyl ether (see EXAMPLE 8) and triethylene glycol monomethyl ether the corresponding mass modified deoxythymidine is prepared. The mass difference between the ethylene, diethylene and triethylene glycol derivatives is 44.05, 88.1 and 132.15 dalton respectively.

EXAMPLE 12

Synthesis of deoxyuridine-5'-triphosphate mass-modified at C-5 of the heterocyclic base with glycine, glycyl-glycine and β-alanine residues.

0.281 g (1.0 mmole) 5-(3-Aminopropynyl-1)-2'-deoxyuridine (see EXAMPLE 5) is reacted with either 0.927 g (2.0 mmole) N-Fmoc-glycine pentafluorophenylester or 0.955 g (2.0 mmole) N-Fmoc-β-alanine pentafluorophenyl ester in 5 ml dry DMF in the presence of 0.129 g N,N-diisopropylethylamine (174 ul, 1.0 mmole) overnight at room temperature. Solvents are removed by evaporation in vacuo and the condensation products purified by flash chromatography on silica gel [Still et al., J. Org. Chem., 43, 2923–2925 (1978)]. Yields: 476 mg (0.85 mmole: 85%) for the glycine and 436 mg (0.76 mmole; 76%) for the .-alanine derivative. For the synthesis of the glycyl-glycine derivative the Fmoc group of 1.0 mmole Fmoc-glycine-deoxyuridine derivative is removed by one-hour treatment with 20% piperidine in DMF at room temperature. Solvents are removed by evaporation in vacuo, the residue is co-evaporated twice with toluene and condensed with 0.927 g (2.0 mmole) N-Fmoc-glycine pentafluorophenyl ester and purified following standard protocol. Yield: 445 mg (0.72 mmole; 72%). The glycyl-, glycyl-glycyl- and β-alanyl-2'-deoxyuridine derivatives N-protected with the Fmoc group are now transformed to the 3'-O-acetyl derivatives by tritylation with 4,4-dimethoxytrityl chloride in pyridine and acetylation with acetic anhydride in pyridine in a one-pot reaction and subsequently detritylated by one-hour treatment with 80% aqueous acetic acid according to standard procedures. Solvents are removed, the residues dissolved in 100 ml chloroform and extracted twice with 50 ml 10% sodium bicarbonate and once with 50 ml water, dried with sodium sulfate, the solvent evaporated and the residues purified by flash chromatography on silica gel. Yields: 361 mg (0.60 mmole; 71%) for the glycyl-, 351 mg (0.57 mmole; 75%) for the .-alanyl- and 323 mg (0.49 mmole; 68%) for the glycyl-glycyl-3-O'-acetyl-2'-deoxyuridine derivatives respectively. Phosphorylation at the 5'-OH with $POCl_3$, transformation into the 5'-triphosphate by in-situ reaction with tetra(tri-n-butylammonium) pyrophosphate in DMF, 3'-de-O-acetylation and cleavage of the Fmoc group and final purification by artion-exchange chromatography on DEAE-Sephadex is performed. Yields according to UV-absorbance of the uracil moiety: 5-(3-(N-glycyl)-amidopropynyl-1)-2'-deoxyuridine-5'-trip hosphate 0.41 mmole (84%), 5-(3-(N-.-alanyl)-amidopropynyl-1)-2'-deoxyuridine-5'-triphosphate 0.43 mmole (75%) and 5-(3-(N-glycyl-glycyl)-amidopropynyl-1)-2'-deoxyuridine-5'-triphosphate 0.38 mmole (78%).

EXAMPLE 13

Synthesis of 8-glycyl- and 8-glycyl-glycyl-2'-deoxyadenosine-5'-triphosphate. 727 mg(1.0 mmole) of N6-(4-tert.butylphenoxyacetyl)-8-glycyl-5'-(4,4-dimethoxytrityl)-2'-deoxyadenosine or 800 mg (1.0 mmole) N6-(4-tert.butylphenoxyacetyl)-8-glycyl-glycyl-5'-(4,4-dimethoxytrityl)-2'-deoxyadenosine prepared according to EXAMPLES 9 and 10 and literature [Koster et al., *Tetrahedron*, 37: 362 (1981)] are acetylated with acetic anhydride in pyridine at the 3'-OH, detritylated at the 5'-position with 80% acetic acid in a one-pot reaction and transformed into the 5'-triphosphates via phosphorylation with $POCl_3$ and reaction in-situ with tetra(tri-n-butylammonium) pyrophosphate. Deprotection of the N6-tert-butylphenoxyacetyl, the 3'-O-acetyl and the O-methyl group at the glycine residues is achieved with concentrated aqueous ammonia for three hours at room temperature. Ammonia is removed by lyophillization and the residue washed with dichloromethane, solvent removed by evaporation in vacuo and the remaining solid material purified by anion-exchange chromatography on DEAE-Sephadex using a linear gradient of triethylammonium bicarbonate from 0.1 to 1.0M. The nucleoside triphosphate containing fractions (checked by TLC on polyethyleneimine cellulose plates) are combined and lyophillized. Yield of the 8-glycyl-2'-deoxyadenosine-5'-triphosphate (determined by the UV-absorbance of the adenine moiety) is 57% (0.57 mmole); the yield for the 8-glycyl-glycyl-2'-deoxyadenosine-5'-triphosphate is 51% (0.51 mmole).

All of the above-cited references and publications are hereby incorporated by reference.

Equivalents

Those skilled in the art will recognize, or be able to ascertain using no more than routine experimentation, numerous equivalents to the specific procedures described herein. Such equivalents are considered to be within the scope of this invention and are covered by the following claims.

---

What is claimed is:

1. A method of determining a sequence of a nucleic acid, comprising the steps of:
(i) obtaining multiple copies of the nucleic acid to be sequenced:
(ii) cleaving the multiple copies from a first end to a second end with an exonuclease to sequentially release individual nucleotides;
(iii) identifying each of the sequentially released nucleotides by mass spectrometry; and
(iv) determining the sequence of the nucleic acid from the identified nucleotides.

2. The method of claim 1, wherein the nucleic acid is a 2'-deoxyribonucleic acid (DNA).

3. The method of claim 1, wherein the nucleic acid is a ribonucleic acid (RNA).

4. The method of claim 1, wherein the exonuclease is selected from the group consisting of snake venom phosphodiesterase, spleen phosphodiesterase, Bal-31 nuclease, E. coli exonuclease I, E. coli exonuclease VII, Mung Bean Nuclease, S1 Nuclease, an exonuclease activity of E. coli DNA polymerase 1, an exonuclease activity of a Klenow fragment of DNA polymerase 1, an exonuclease activity of T4 DNA polymerase, an exonuclease activity of T7 DNA polymerase, an exonuclease activity of Taq DNA polymerase, an exonuclease activity of DEEP VENT DNA polymerase, E. coli exonuclease III, λ exonuclease and an exonuclease activity of VENT$_R$ DNA polymerase.

5. The method according to claim 1, wherein the exonuclease is immobilized by covalent attachment to a solid support, entrapment within a gel matrix, or contained in a reactor with a semipermeable membrane.

6. The method according to claim 5, wherein the solid support is a capillary and the exonuclease activity is covalently attached to an inner wall of the capillary.

7. The method according to claim 5, wherein the solid support is selected from the group consisting of glass beads, cellulose beads, polystyrene beads, SEPHADEX beads, SEPHAROSE beads, polyacrylamide beads and agarose beads.

8. The method according to claim 5, wherein the solid support is a flat membrane.

9. The method according to claim 1, wherein the nucleic acid is immobilized by covalent attachment to a solid support and the exonuclease is in a solution and is contacted with the immobilized nucleic acid.

10. The method according to claim 9, wherein the solid support is a capillary and the nucleic acid is covalently attached to an inner wall of the capillary.

11. The method according to claim 9, wherein the solid support is selected from the group consisting of glass beads, cellulose beads, polystyrene beads, SEPHADEX beads, SEPHAROSE beads, polyacrylamide beads and agarose beads.

12. The method according to claim 9, wherein the solid support is a flat membrane.

13. The method according to claim 1, wherein the nucleic acid comprises mass-modified nucleotides.

14. The method according to claim 13, wherein the mass-modified nucleotides modulate the rate of the exonuclease activity.

15. The method according to claim 1, wherein the sequentially released nucleotides are mass-modified subsequent to exonuclease release and prior to mass spectrometric identification.

16. The method according to claim 15, wherein the sequentially released nucleotides are mass-modified by contact with an alkaline phosphatase.

17. The method according to claim 9, wherein the nucleic acid further comprises a linking group (L) for covalently attaching the nucleic acid to the solid support.

18. The method according to claim 17, wherein the solid support further comprises a splint oligonucleotide and the linking group (L) comprises a nucleotide sequence able to anneal to the splint oligonucleotide and be covalently attached to the solid support by action of a ligase.

19. A method of claim 1, wherein the mass spectrometry format used in step (iii) is matrix assisted laser desorption (MALDI) mass spectrometry or electrospray (ES) mass spectrometry.

20. A method of determining a sequence of a nucleic acid, comprising the steps of:
   (i) obtaining multiple copies of the nucleic acid to be sequenced;
   (ii) cleaving the multiple copies from a first end to a second end with an exonuclease to produce multiple sets of nested nucleic acid fragments;
   (iii) determining the molecular weight value of each one of the sets of nucleic acid fragments by mass spectrometry; and
   (iv) determining the sequence of the nucleic acid from the molecular weight values of the sets of nucleic acid fragments.

21. The method of claim 20, wherein the nucleic acid is a 2'-deoxyribonucleic acid (DNA).

22. The method of claim 20, wherein the nucleic acid is a ribonucleic acid (RNA).

23. The method of claim 20, wherein the exonuclease is selected from the group consisting of snake venom phosphodiesterase, spleen phosphodiesterase, Bal-31 nuclease, *E. coli* exonuclease I, *E. coli* exonuclease VII, Mung Bean Nuclease, S1 Nuclease, an exonuclease activity of *E. coli* DNA polymerase I, an exonuclease activity of a Klenow fragment of DNA polymerase I, an exonuclease activity of T4 DNA polymerase, an exonuclease activity of T7 DNA polymerase, an exonuelease activity of Taq DNA polymerase, an exonuclease activity of DEEP VENT DNA polymerase, *E. coli* exonuclease III, λ exonuclease and an exonuclease activity of $VENT_R$ DNA polymerase.

24. The method of claim 20, wherein the exonuclease is immobilized by covalent attachment to a solid support, entrapment within a gel matrix, or contained in a reactor with a semipermeable membrane.

25. The method of claim 20, wherein the nucleic acid is immobilized by covalent attachment to a solid support and the exonuclease is in a solution contacted with the immobilized polynucleotide.

26. The method of claim 20, wherein the nucleic acid comprises mass-modified nucleotides.

27. The method of claim 26, wherein the exonucleolytically degraded nucleic acid is mass-modified subsequent to exonuclease treatment and prior to mass spectrometric identification.

28. A method of claim 20, wherein the mass spectrometry format used in step (iii) is matrix assisted laser desorption (MALDI) mass spectrometry or electrospray (ES) mass spectrometry.

* * * * *